United States Patent [19]
Goldstein et al.

[11] Patent Number: 5,618,493
[45] Date of Patent: Apr. 8, 1997

[54] PHOTON ABSORBING BIODERIVED ORGANOMETALLIC CARBON MONOXIDE SENSORS

[75] Inventors: Mark K. Goldstein, Del Mar; Michelle S. Oum; Kathleen L. Kerns, both of San Diego, all of Calif.

[73] Assignee: Quantum Group, Inc., San Diego, Calif.

[21] Appl. No.: 297,141

[22] Filed: Aug. 29, 1994

[51] Int. Cl.⁶ .......................... G01N 21/01; G01N 31/22
[52] U.S. Cl. .................... 422/57; 73/31.02; 73/31.03; 73/31.05; 422/82.05; 422/82.09; 422/88; 422/91; 436/134
[58] Field of Search .............................. 436/169, 81, 128, 436/902; 422/58, 88, 91, 57, 82.05, 82.09; 428/402.4; 252/315.2; 73/31.01–31.03, 31.05

[56] References Cited

U.S. PATENT DOCUMENTS

| | | | |
|---|---|---|---|
| 4,043,934 | 8/1977 | Shuler et al. | 252/186 |
| 5,063,164 | 11/1991 | Goldstein | 436/169 |
| 5,302,350 | 4/1994 | Goswami et al. | 422/86 |
| 5,319,975 | 6/1994 | Pederson et al. | 422/83 |
| 5,346,671 | 9/1994 | Goswami . | |
| 5,405,583 | 4/1995 | Goswami et al. | 422/86 |

OTHER PUBLICATIONS

Martin Sheperd; "Rapid Determination of Small Amounts of Carbon Monoxide" *Analytical Chemistry* 19 (1947) pp. 77–81.

*Primary Examiner*—Jill Warden
*Assistant Examiner*—Jan M. Ludlow
*Attorney, Agent, or Firm*—Christie, Parker & Hale, LLP

[57] ABSTRACT

An improved carbon monoxide sensor system has a dual sensor system having two sensors disposed in a series arrangement within a sensor housing. Each sensor is formed from a porous semi-transparent substrate that is impregnated with a different chemical sensor reagent. At lease one sensor substrate surface is treated with a chemical compound before being impregnated to increase average pore size and, thereby, increase the sensitivity of the sensor. One sensor is formed from a chemical sensor reagent designed to perform at a lower to middle humidity and temperature range. The other sensor is formed from a chemical sensor reagent designed to perform at a middle to high humidity and temperature range. The dual sensor system constructed in this manner provides good carbon monoxide sensitivity at temperature and humidity conditions required by the standards of UL-2034.

31 Claims, 10 Drawing Sheets

High Humidity/High Temperature Test

Accelerated Aging Test

Standard CO Test

PHOTON ABSORBING BIODERIVED ORGANOMETALLIC CARBON MONOXIDE SENSORS

FIELD OF INVENTION

The present invention relates to an improved device for detecting the presence of carbon monoxide by means of two solid-state bioderived organometallic sensors.

BACKGROUND OF THE INVENTION

Airborne gases and vapors, such as carbon monoxide and mercury, are often difficult to detect; they may be colorless and odorless or toxic at levels below which they can be seen or smelled by an average person. Hydrogen sulfide ($H_2S$) can be detected by the nose at the parts per billion level. However, if one has been exposed to high levels of $H_2S$ the nose becomes desensitized to the chemical and can no longer detect it at such low levels. Also, in many environments, the smell of certain gases may be masked by other odors that are present in the air. These airborne material toxins present a growing danger to humans in automobiles, airplanes, industrial plants, mines, homes, and other environments in which humans are present for extended periods of time.

Chemical sensors, for detecting the presence of gases and vapors have been in use for many years. For example, the use of palladium and molybdenum salts for carbon monoxide detection is described in *Analytical Chemistry*, Vol. 19, No. 2, pages 77–81 (1974). K. Shuler and G. Schrauzer improved upon this technology by adding a third metallic salt component which produced a self-regenerating, short-lived catalyst. This catalyst, disclosed in U.S. Pat. No. 4,043,934, uses the impregnation of a carbon monoxide-sensitive catalyst solution onto powdered silica-gel substrates to produce detectors that are sensitive to low concentrations of atmospheric carbon monoxide. However, while this system is effective in detecting carbon monoxide, it has not met with commercial acceptance due to the short functional life of the sensor.

U.S. Pat. No. 5,063,164 disclosed a method to allow the carbon monoxide sensor system to be useful in consumer products, i.e. operate for at least one year without maintenance or calibration. However, the formulations disclosed in U.S. Pat. No. 5,063,164 do not pass UL 2034 standards published on Apr. 30, 1992 with respect to sensitivity and false alarm under all conditions, and specifically, under conditions of high humidity, without further modifications. The sensors disclosed in U.S. Pat. No. 5,063,164 are characterized as having a low sensitivity to carbon monoxide, a slow regeneration time, and respond in a narrow humidity range.

It is, therefore, desirable that a carbon monoxide sensor system be constructed having sensors that are formulated to provide improved sensitivity, quicker regeneration, and response in a wider humidity range than known carbon monoxide sensor systems. It is desirable that the carbon monoxide sensors meet or exceed required UL 2034 standards and have an extended functional life of at least three years normal operation.

UL Standard 2034 as published Apr. 30, 1992, contains the following criteria for a carbon monoxide sensor:

Criterion 1: Preconditioning for about 48 hours in a controlled atmosphere of about 20°–25° C. and about 85±5% relative humidity followed by exposure to about 200 parts per million carbon monoxide for about 35 minutes after which the ratio of light transmitted through the sensor system before the exposure to carbon monoxide to light transmitted through the sensor system immediately after exposure to carbon monoxide is equal to or greater than about 2:1;

Criterion 2: Preconditioning for about 3 hours in a controlled atmosphere of about 20°–25° C. and about 15±5% relative humidity followed by exposure to about 200 parts per million carbon monoxide for about 35 minutes after which the ratio of light transmitted through the sensor system before exposure to carbon monoxide to light transmitted through the sensor system immediately after exposure to carbon monoxide is equal to or greater than about 2:1;

Criterion 3: Preconditioning for about 24 hours in a controlled atmosphere of about 20°–25° C. and 53±3% relative humidity followed by exposure to about 15–20 parts per million carbon monoxide for about 8 hours in a controlled atmosphere of about 20°–25° C. and about 53±3% relative humidity after which the ratio of light transmitted through the sensor system before exposure to carbon monoxide to light transmitted through the sensor immediately after exposure to carbon monoxide is equal to or less than about 1:1;

Criterion 4: Preconditioning for about 168 hours in a controlled atmosphere of about 52° C. and about 95% relative humidity followed by exposure to about 400 parts per million carbon monoxide for about 15 minutes in a controlled atmosphere of about 20°–25° C. and about 53±3% relative humidity after which the ratio of light transmitted through the sensor system before exposure to carbon monoxide to light transmitted through the sensor system immediately after exposure to carbon monoxide is equal to or greater than about 2:1;

Criterion 5: Preconditioning for about 240 hours in a controlled atmosphere of about 61° C. and about 93% relative humidity followed by about 3 hours in a controlled atmosphere of about 61° C. and about 85% relative humidity followed in turn by exposure to about 400 parts per million carbon monoxide for about 15 minutes in a controlled atmosphere about 61° C. and about 85% relative humidity after which the ratio of light transmitted through the sensor system before exposure to carbon monoxide to light transmitted through the sensor system immediately after exposure to carbon monoxide is greater than or equal to about 2:1;

Criterion 6: Preconditioning for about 30 days in a controlled atmosphere of about 70° C. and a low relative humidity followed by a decrease in temperature to about 49° C. and a relative humidity of about 50±20% relative humidity for about 1 hour followed in turn by exposure to about 200 parts per million carbon monoxide for about 35 minutes after which the ratio of light transmitted through the sensor system before exposure to carbon monoxide to light transmitted through the sensor system immediately after exposure to carbon monoxide is equal to or greater than about 2:1;

Criterion 7: Preconditioning for about 72 hours in a controlled atmosphere of −40° C. and a low relative humidity followed by an increase in the temperature to 0° C. and 15±5% relative humidity and exposure to 200 parts per million carbon monoxide for about 35 minutes after which the ratio of light transmitted through the sensor system before exposure to carbon monoxide to light transmitted through the sensor system immediately after exposure to carbon monoxide is greater than or equal to about 2:1;

Criterion 8: Preconditioning for about 24 hours in a controlled atmosphere of about 20°–25° C. and 53±2% relative humidity followed by exposure to about 100 parts per million carbon monoxide for about 80 minutes under ambient conditions after which the ratio of light transmitted through the sensor system before exposure to carbon monoxide to light transmitted through the sensor system immediately after exposure to carbon monoxide is greater than or equal to about 2:1;

Criterion 9: Preconditioning for about 48 hours in a controlled atmosphere of about 20°–25° C. and about 85±5% relative humidity followed by exposure to 200 parts per million carbon monoxide for about 35 minutes followed in turn by exposure for about 24 hours to an atmosphere of carbon monoxide free air after which the difference between the light transmitted through the sensor system after exposure to carbon monoxide free air and the light transmitted through the sensor system after exposure to carbon monoxide is divided by the difference between the light transmitted through the sensor system before exposure to carbon monoxide and the light transmitted through the sensor system after exposure to carbon monoxide, the quotient then being multiplied by 100 and the final result having a value greater than or equal to about 90.

SUMMARY OF THE INVENTION

A carbon monoxide sensor system prepared according to principles of this invention is a dual sensor system comprising a first sensor and a second sensor disposed within a sensor housing. Each first and second sensor are formed from a porous transparent or semi-transparent substrate that is sufficiently transmissive to light to permit detection of light transmitted through the sensors by the human eye or by a photodiode or the like. Each substrate is impregnated with a chemical reagent that is formulated to decrease the degree of light transmittance through the sensor in relation to an increasing concentration of carbon monoxide.

Each substrate forming each different sensor is impregnated with a different chemical reagent for purposes of providing good carbon monoxide sensitivity at different temperature and humidity conditions as required by the standards of UL-2034. The substrate forming the second sensor is treated with a chemical compound to increase the average pore diameter from 3 to 10 nanometers ($3\times10^{-7}$ to $1\times10^{-6}$ centimeters) to greater than 15 nanometers ($1.5\times10^{-6}$ centimeters), thereby increasing the surface area of the substrate and the sensitivity of the sensor.

A chemical reagent that is used to form the first sensor is the same as that disclosed in U.S. Pat. No. 5,063,164. A chemical reagent that is used to form the second sensor is formed from a mixture of at least one of the compounds from each of the following groups:

Group 1: Palladium salts selected from the group including palladium sulfate, palladium sulfite, palladium pyrosulfite, palladium chloride ($PdCl_2$), palladium bromide ($PdBr_2$), palladium iodide, palladium perchlorate, $CaPdCl_4$, $Na_2PdCl_4$, $K_2PdCl_4$, $PdCl_2.2H_2O$, $PdBr_2.2H_2O$, $K_2PdBr_4$, $Na_2PdBr_4$, $PdCl_2Br^{-2}$, $PdCl_3Br$, $PdClBr_3^{-2}$, or mixtures thereof;

Group 2: Molybdenum selected from the group including silicomolybdic acid, salts of silicomolybdic acid, molybdenum trioxide, heteropolyacids of molybdenum containing vanadium, copper, or tungsten, ammonium molybdate, alkali metal or alkaline earth salts of the molybdate anion, heteropolymolybdates, or mixtures thereof;

Group 3: Copper salts selected from the group including copper sulfate, copper bromide, copper chloride, copper fluoride, copper iodide, copper trifluoroacetate, and copper perchlorate;

Group 4: Molecular encapsulants selected from the group including α-cyclodextrin, β-cyclodextrin, modified β-cyclodextrin, γ-cyclodextrin, other modified cyclodextrins, or combinations thereof;

Group 5: Soluble chloride and bromide ions selected from the group including lithium, sodium, aluminum, platinum, calcium, magnesium, and cobalt chlorides and bromides, or mixtures thereof; and Group 6: An organic solvent and trifluorinated organic anion, the solvent selected from the group including dimethyl sulfoxide (DSMO), tetrahydrofuran (THF), dimethyl formamide (DMF), trichloroacetic acid, and the anion is a soluble metal trifluoroacetylacetonate selected from the cation group consisting of copper, calcium, magnesium, sodium, potassium, and lithium, or mixtures thereof.

Upon exposure of the chemical sensor system to air containing carbon monoxide, the chemical sensors undergo changes in their optical density. These changes in the optical density are adequate to meet the UL 2034 standard with respect to sensitivity and false alarm, at a cost nearly comparable to photoelectric smoke detectors. The sensor system constructed in accordance with the principles of this invention displays an increased sensitivity to carbon monoxide and a longer functional life at high humidity.

BRIEF DESCRIPTION OF THE DRAWINGS

These and other features and advantages of the present invention will become appreciated as the same becomes better understood with reference to the specification, claims and drawings wherein:

DETAILED DESCRIPTION OF THE INVENTION

Figure 1:
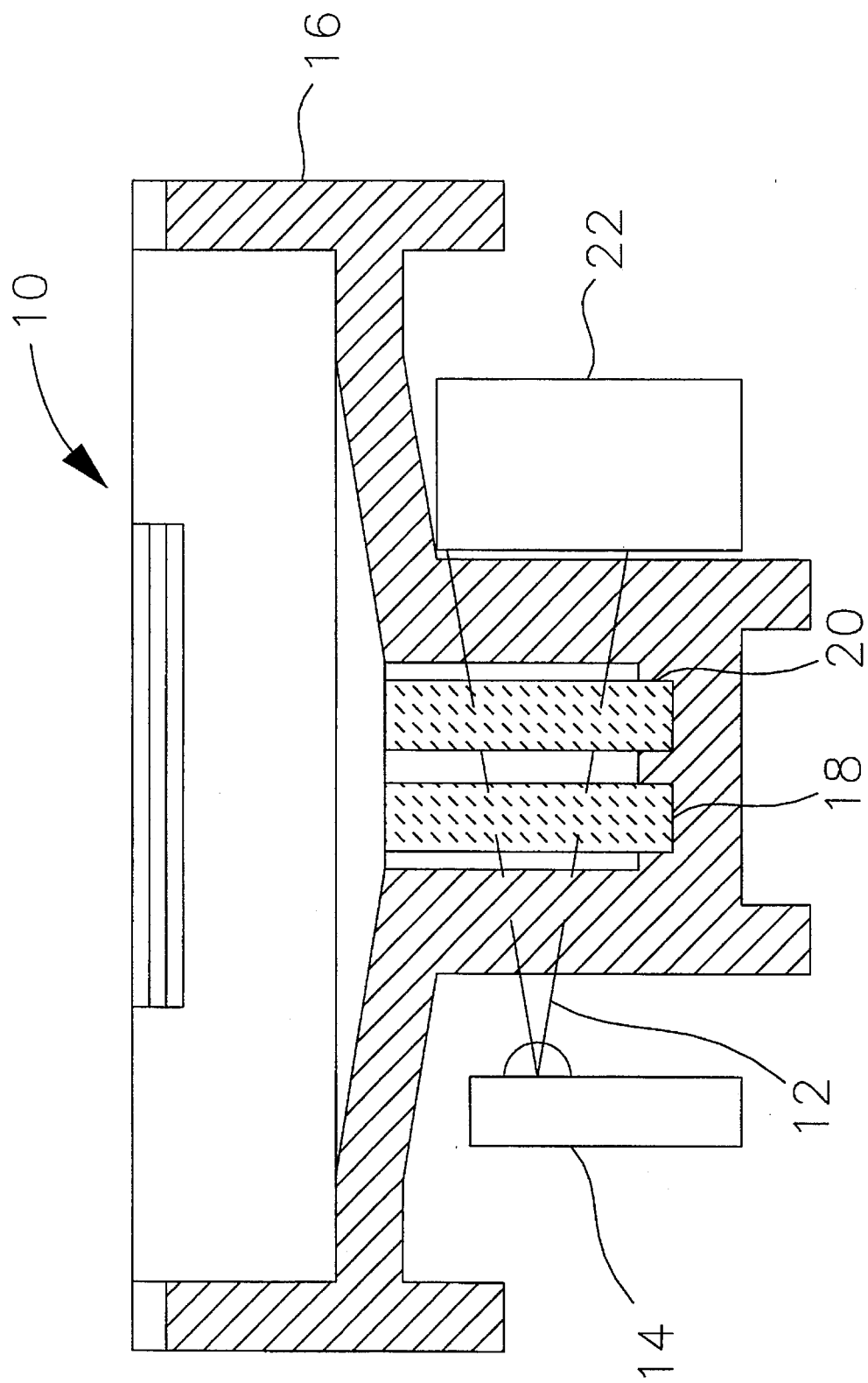
FIG. 1 is a schematic view of a carbon monoxide detector incorporating carbon monoxide sensors constructed according to principles of this invention.
Figure 2:
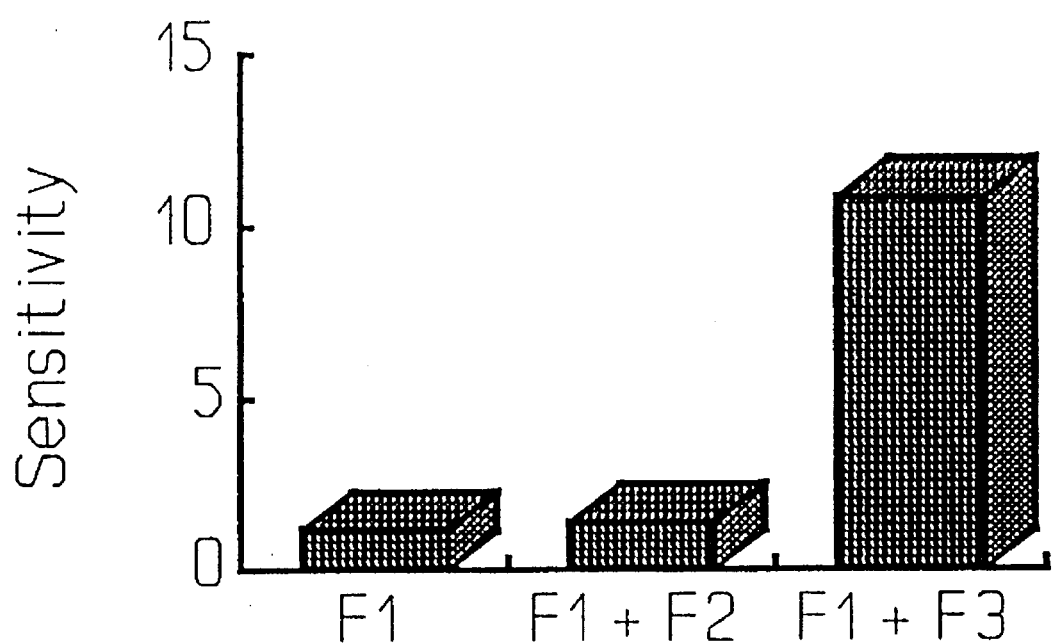
FIG. 2 is a chart illustrating in graphical form a comparison of carbon monoxide sensitivities for three different carbon monoxide sensor formulations provided in Table 1 and subjected to 200 ppm carbon monoxide at approximately 85 percent relative humidity.
Figure 3:
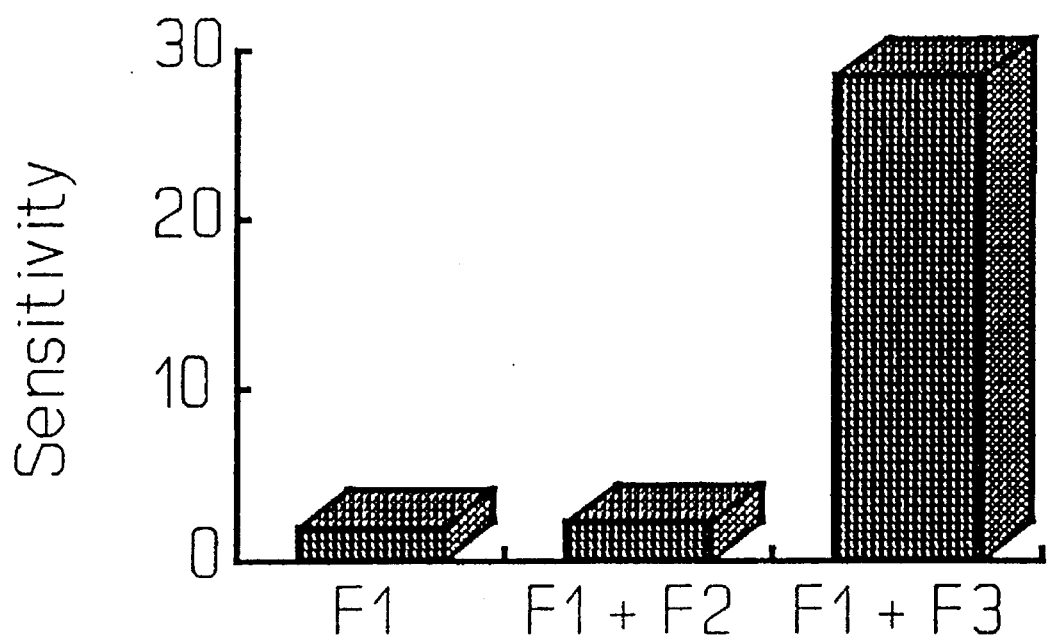
FIG. 3 is a chart illustrating in graphical form a comparison of carbon monoxide sensitivities for three different carbon monoxide sensor formulations provided in Table 2 and subjected to 200 ppm carbon monoxide at approximately 15 percent relative humidity.
Figure 4:
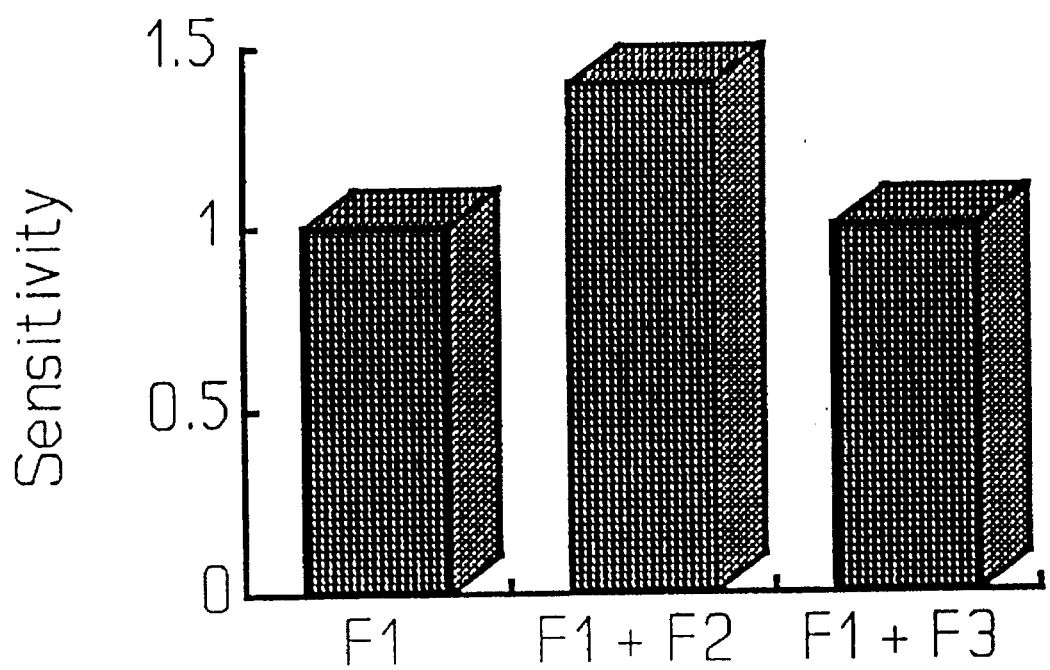
FIG. 4 is a chart illustrating in graphical form a comparison of carbon monoxide sensitivities for three different carbon monoxide sensor formulations provided in Table 3 and subjected to 15–20 ppm carbon monoxide at approximately 53 percent relative humidity.
Figure 5:
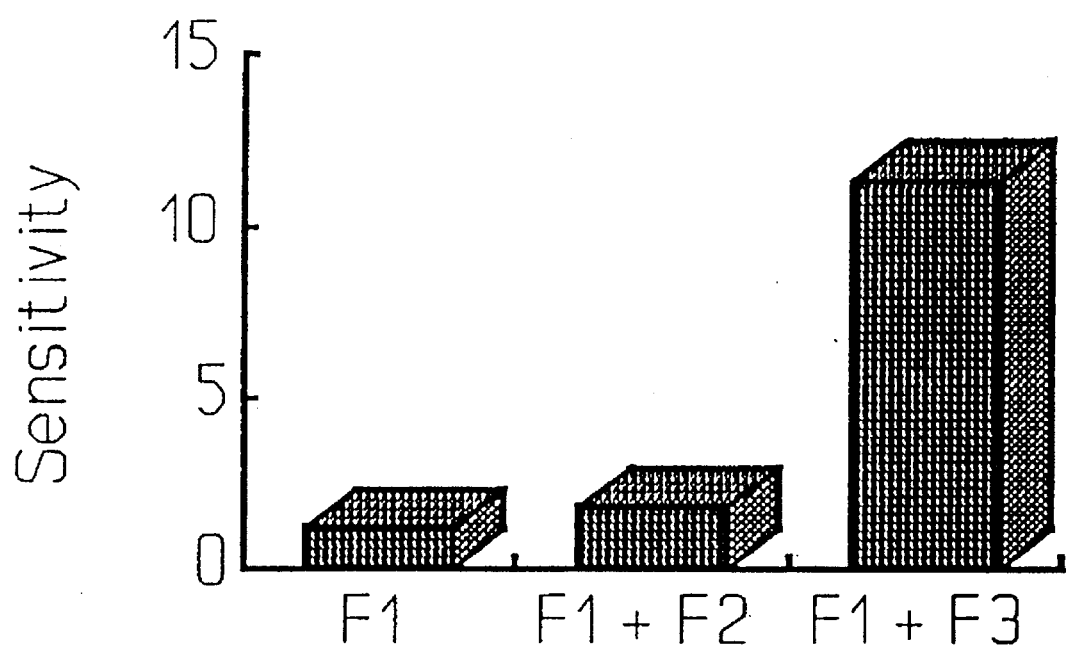
FIG. 5 is a chart illustrating in graphical form a comparison of carbon monoxide sensitivities for three different carbon monoxide sensor formulations provided in Table 4 and subjected to 400 ppm carbon monoxide at approximately 95 percent relative humidity.
Figure 6:
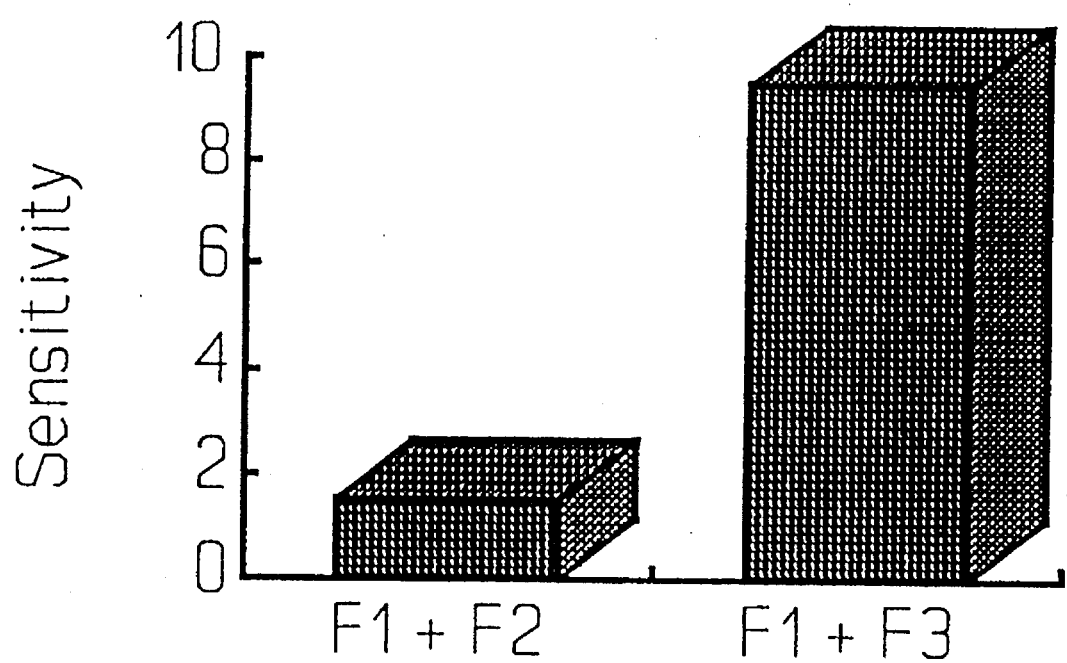
FIG. 6 is a chart illustrating in graphical form a comparison of carbon monoxide sensitivities for three different carbon monoxide sensor formulations provided in Table 5 and subjected to 400 ppm carbon monoxide at approximately 85 percent relative humidity.
Figure 7:
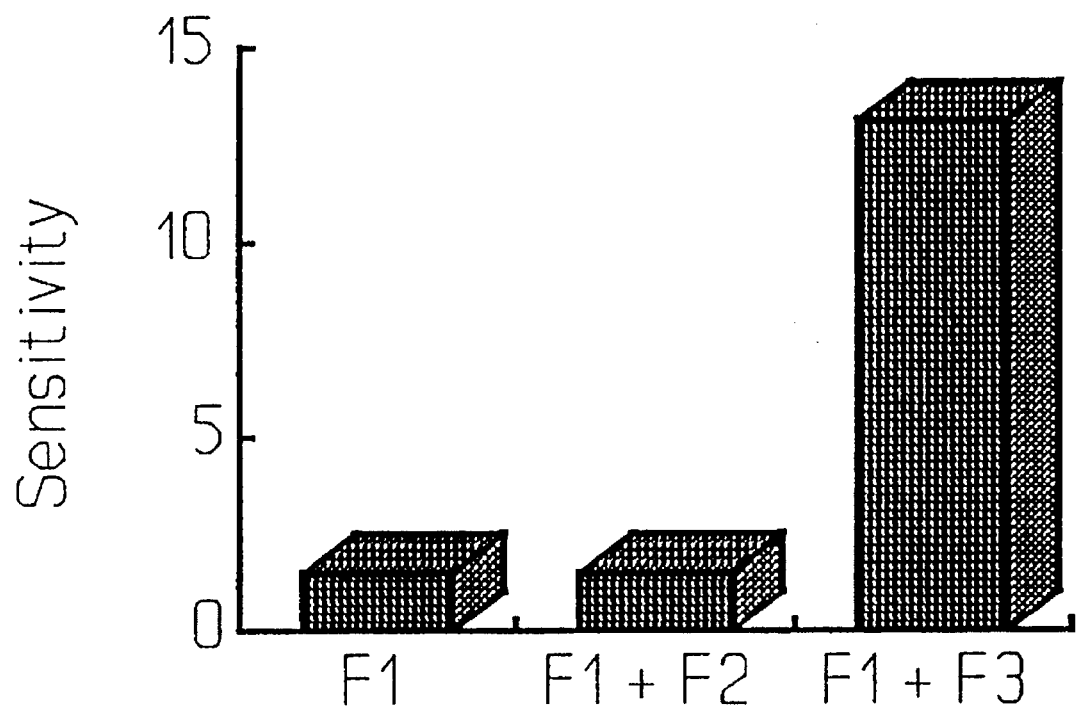
FIG. 7 is a chart illustrating in graphical form a comparison of carbon monoxide sensitivities for three different carbon monoxide sensor formulations provided in Table 6 and subjected to 200 ppm carbon monoxide at approximately 50 percent relative humidity.
Figure 8:
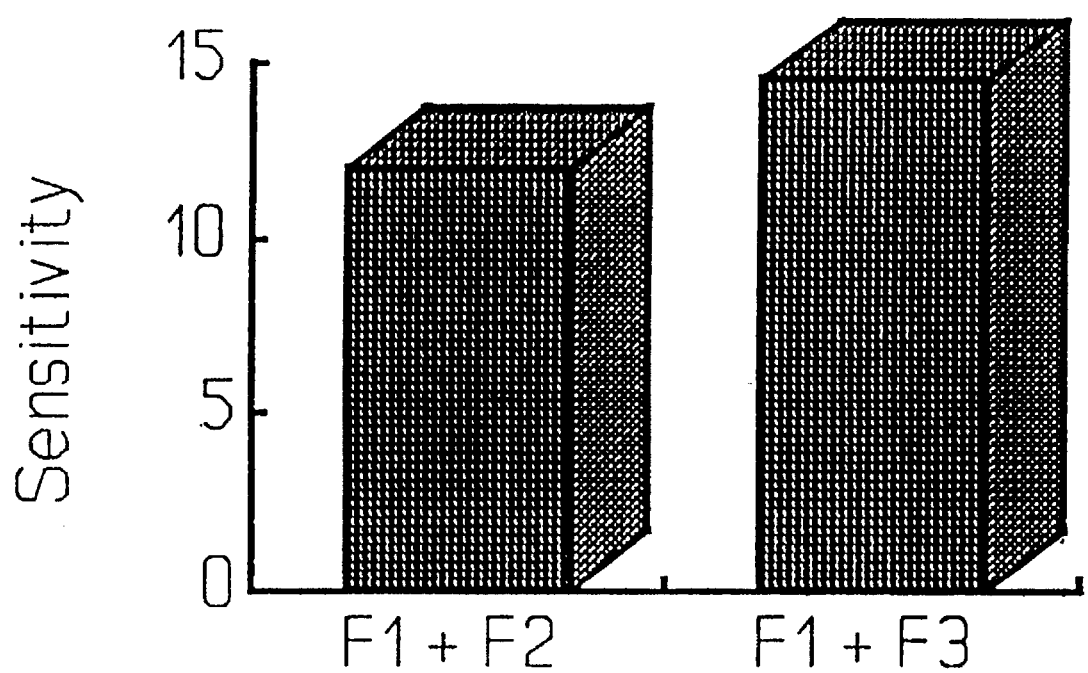
FIG. 8 is a chart illustrating in graphical form a comparison of carbon monoxide sensitivities for three different carbon monoxide sensor formulations provided in Table 7 and subjected to 200 ppm carbon monoxide at approximately 15 percent relative humidity.
Figure 9:
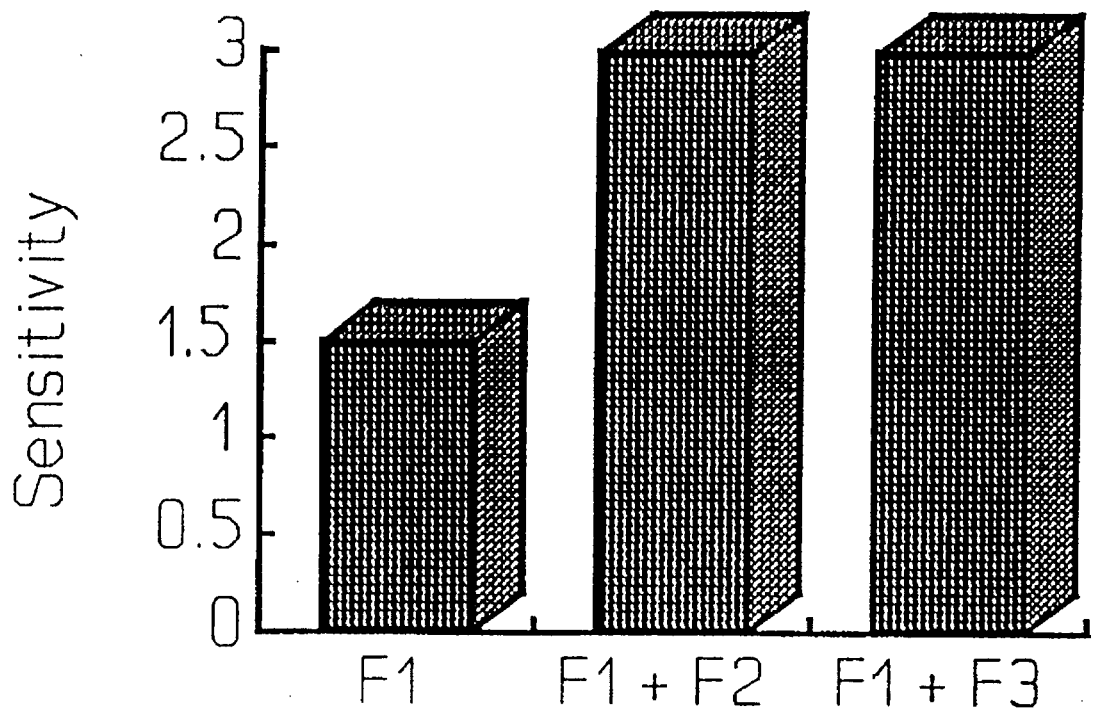
FIG. 9 is a chart illustrating in graphical form a comparison of carbon monoxide sensitivities for three different carbon monoxide sensor formulations provided in Table 8 and subjected to 100 ppm carbon monoxide at approximately 53 percent relative humidity.
Figure 10:
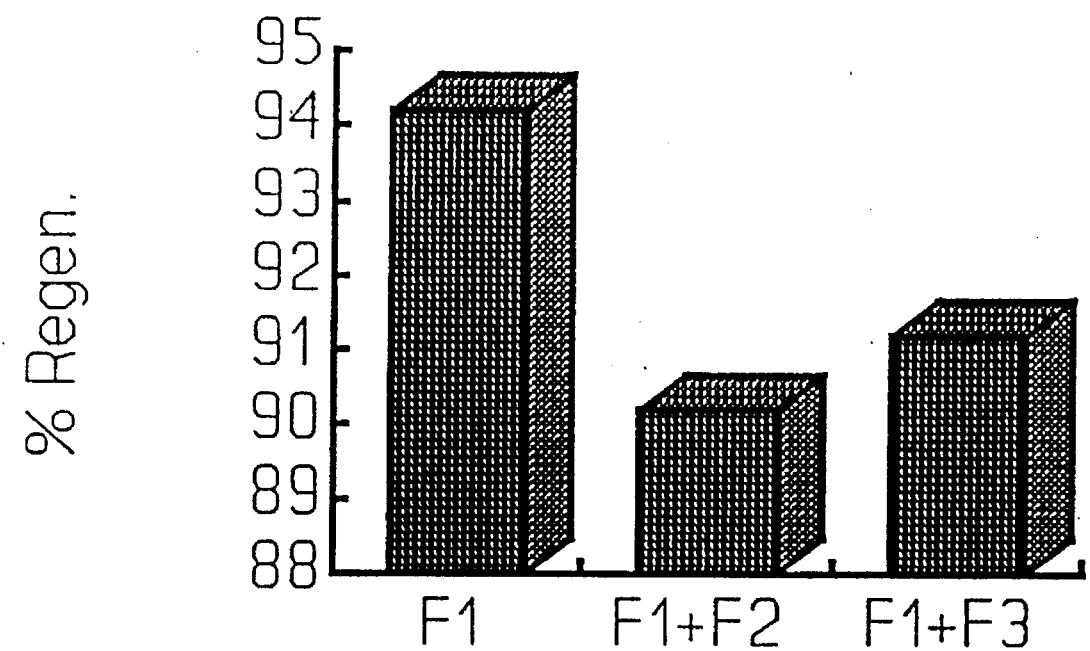
FIG. 10 is a chart illustrating in graphical form a comparison of regeneration rates provided in Table 9 for the three different carbon monoxide sensor formulations provided in Table 2.

The present invention comprises of an improved chemical sensor system for detecting the presence of carbon monoxide (CO) and other gaseous chemicals (i.e. hydrogen sulfide ($H_2S$) and the like). The chemical sensor system constructed according to principles of this invention is an improvement over the single sensor system disclosed in U.S. Pat. No. 5,063,164, which is herein incorporated by reference, which is made possible by the use of additional sensor. FIG. 1 illustrates a chemical detector 10 incorporating a new chemical sensor system constructed according to principles of this invention. Light 12 is emitted by an infrared light emitting diode (LED) 14 positioned adjacent a sensor housing 16. The light 12 passes in series through a first sensor 18 and a second sensor 20 contained within the housing 16. The light passing through both the first and second sensor is transmitted to a photodiode 22. When the first and second sensors 18 and 20 are exposed to CO they darken, thereby reducing the amount of light transmitted. When the light transmittance registered by the photodiode 20 is reduced to a certain setpoint, corresponding to a predetermined level of chemical gas (i.e., carbon monoxide) present in the air, an alarm (not shown) is triggered.

Each of the sensors 18 and 20 in this invention are made from distinctly different substrates and self-regenerating sensor reagents. As noted in FIG. 1, the first sensor 18 is that disclosed in U.S. Pat. No. 5,063,164 (Formula #1) and is initially yellow in color, but turns green to dark blue upon exposure to CO. The first sensor 18 performs at the lower to middle humidity and temperature range. The second sensor 20 may comprises either the same substrate and a modified version of the chemical sensor reagent used in U.S. Pat. No. 5,063,164, (Formula #2) or modified versions of both the substrate and the chemical sensor reagent used in the above-mentioned patent (Formula #2). The second sensor 20 is initially red-orange in color and turns dark red to black upon exposure to CO, and performs at the middle to high humidity and temperature range.

Accordingly, a dual sensor system comprising a first sensor that performs best at low to middle humidity and second sensor that performs best at a middle to high humidity enables the system to monitor both extremes of temperature and humidity as required by UL 2034, an effect which cannot be accomplished with a single sensor system, or a dual sensor system comprising sensors of the same type.

A brief summary describing the first sensor 18 from U.S. Pat. No. 5,063,164 (herein referred to as Formula #1) and a more detailed description of the second sensor (herein referred to as Formula #2 or Formula #3, respectively) follows. [Note: It is important to be aware of an error that exists throughout U.S. Pat. No. 5,063,164. In U.S. Pat. No. 5,063,164, everywhere that the units of nanometers (1 nm=$10^{-9}$ m) are placed after a number, the number should be written with the decimal place moved 2 places to the left. For example, a number written as 35 nanometers should actually read 0.35 nanometers. When comparing/contrasting the improved sensor system in this patent application with the system described in U.S. Pat. No. 5,063,164 it is important to keep this error in mind.]

As disclosed in U.S. Pat. No. 5,063,164, Formula #1 is made from a porous semi-transparent substrate (i.e., the substrate is sufficiently transmissive to light to permit detection of the transmitted light by a photodiode, or the like) that has been impregnated or coated with a self regenerating chemical reagent containing a mixture of at least one of the compounds from each of the following Groups 1–5:

Group 1: Palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2: Molybdenum and/or tungsten salts or acid salts selected from the group consisting of silicomolybdic acid, salts of silicomolybdic acid, molybdenum trioxide, heteropolyacids of molybdenum, ammonium molybdate, alkali metal, or alkaline earth metal salts of the molybdate anion, mixed heteropolymolybdates, or heteropolytungstates;

Group 3: Copper salts selected from the group consisting of copper sulfate, copper chloride, copper bromide, copper iodide, and copper perchlorate;

Group 4: Molecular encapsulants that encapsulate at least one but not all components of the chemical reagent system, selected from the group that includes, but is not limited to, α-cyclodextrin, β-cyclodextrin, modified β-cyclodextrin, and γ-cyclodextrin, and which has an internal cavity with a diameter of at least 0.50 nanometers ($5 \times 10^{-8}$ centimeters); and Group 5: Soluble chloride ions selected from the group consisting of lithium chloride, sodium chloride, lithium perchlorate, aluminum perchlorate, platinum chloride, inorganic acids, calcium chloride, magnesium chloride, cobalt chloride, or mixtures thereof.

The mole ratio ranges for the components of the reagent solution used to form the first sensor are as follows:

Group 1:Group 2=0.01:1 to 0.5:1;

Group 3:Group 2=0,001:1 to 0.08:1;

Group 4:Group 2=1:1 to 20:1;

Group 5:Group 2=0.01:1 to 10:1;

The substrate used to form the first sensor 18 is chosen from, but is not limited to, materials from the following list; commercial silica-gel desiccants in bead form (available from most major suppliers of silica-gel), porous silicon dioxide such as GELSIL® made by Geltech of Alachua, Fla., and porous, leached, borosilicate glass such as VYCOR® ("THIRSTY GLASS," Corning Glass Works, Corning, N.Y. Brand No. 7930. A variety of physical shapes and forms for the substrate are obtained by suitable commercial processes.

Formula #2, i.e., the chemical reagent used to form the second sensor 20 is prepared by using the same substrate as that previously disclosed in Formula #1. The substrate is impregnated with a chemical reagent that comprises a mixture of at least one of the compounds from each of the following Groups 1–6:

Group 1: Palladium salts selected from the group including palladium sulfate, palladium sulfite, palladium pyrosulfite, palladium chloride ($PdCl_2$), palladium bromide ($PdBr_2$), palladium iodide, palladium perchlorate, $CaPdCl_4$, $Na_2PdCl_4$, $K_2PdCl_4$, $PdCl_2 \cdot 2H_2O$, $PdBr_2 \cdot 2H_2O$, $K_2PdBr_4$, $Na_2PdBr_4$, $PdCl_2Br_2^{-2}$, $PdCl_3Br^{-2}$, $PdClBr_3^{-2}$ or mixtures thereof;

Group 2: Molybdenum selected from the group including silicomolybdic acid, salts of silicomolybdic acid, molybdenum trioxide, heteropolyacids of molybdenum containing vanadium, copper, or tungsten, ammonium molybdate, alkali metal or alkaline earth salts of the molybdate anion, heteropolymolybdates, or mixtures thereof;

Group 3: Copper salts selected from the group including copper sulfate, copper bromide, copper chloride, copper fluoride, copper iodide, copper trifluoroacetate, and copper perchlorate;

Group 4: Molecular encapsulants selected from the group including α-cyclodextrin, β-cyclodextrin, modified β-cyclodextrin, γ-cyclodextrin, other modified cyclodextrins, or combinations thereof;

Group 5: Soluble chloride and bromide ions selected from the group including lithium, sodium, aluminum, platinum, calcium, magnesium, and cobalt chlorides and bromides, or mixtures thereof; and Group 6: An organic solvent and trifluorinated organic anion, the solvent selected from the group including dimethyl sulfoxide (DSMO), tetrahydrofuran (THF), dimethyl formamide (DMF), trichloroacetic acid, and the anion is a soluble metal trifluoroacetylacetonate selected from the cation group consisting of copper, calcium, magnesium, sodium, potassium, and lithium, or mixtures thereof.

The mole ratio ranges for the components of the reagent solution used to form the second sensor are as follows:

Group 1:Group 2=0.01:1 to 0.5:1;

Group 3:Group 2=0.001:1 to 0.08:1;

Group 4:Group 2=1:1 to 20:1;

Group 5:Group 2=0.01:1 to 10:1; and

Group 6:Group 2=0.00001:1 to 0.001:1

A preferred chemical sensor reagent solution used to form the second sensor includes a Group 1 compound comprising palladium chloride and $Na_2PdCl_4$, a Group 2 compound comprising silicomolybdic acid, a Group 3 compound comprising copper chloride, a Group 4 compound comprising modified β-cyclodextrin γ-cyclodextrin, a Group 5 compound comprising calcium chloride and calcium bromide, a Group 6 compound comprising trichloroacetic acid and copper trifluoroacetylacetonate.

The substrate used for Formula #3 is similar, although not identical, to the substrate used for Formula #1 and Formula #2. The substrate used to form the second sensor 20 is distinguished by having a larger pore size on its exterior surface and, therefore, is characterized as having a less translucent appearance. The substrate used to form the second sensor 20 is prepared by treating the same substrate material previously disclosed for Formula #1 and Formula #2 with one or more of the following chemical reagents: ammonium bifluoride ($NN_4HF_2$ or $NH_4F \cdot HF$); ammonium fluoride; hydrofluoric acid. The use of such treatment chemicals etches the surface of the substrate, thereby increasing the size of the pore diameter and enhancing the surface area of the substrate. Alternately, substrates of the types previously mentioned for Formulas #1 and #2, in a large pore size form, may be used. The modified substrate is then impregnated with the same chemical sensor reagent mixture disclosed in Formula #2.

The chemical sensor system undergoes a change in its optical density in response to contact with CO. Therefore, the presence of CO can be quantified by comparing the optical density of the chemical sensor system which has been exposed to CO, with the optical density of an unexposed chemical sensor system. This change in the optical density of the chemical sensor system is dependent upon both the concentration of the CO and the time of exposure.

The surface area of each porous transparent or semi-transparent substrate is an important physical property, since surface area is proportional to the reactivity of the chemical sensor system. High surface areas are preferred to maximize the degree of impregnation of the sensor system and, thus, optimize sensitivity. In this regard, very high surface area aerogels and xerogels made by a technology developed at Lawrence Livermore National Laboratory [R2] and Sandia National Laboratory [R3], respectively, have the potential for a significant increase in sensitivity. However, practical limitations occur because of mechanical stability. Chemical sensor systems made with porous monolithic materials remain viable for longer periods of time than sensors made with powdered materials. Also, porous monolithic sensors are less expensive to manufacture and easier to control; therefore, they are more amenable to commercial applications than are powdered silica sensors, electrochemical sensors, and semiconductor sensors.

The pore diameter of the porous transparent or semi-transparent substrate is an important factor, since the pores must be able to accommodate the diffusion of the target gas. A suitable substrate for service as a chemical sensor may have an average pore diameter in the range of from 1.5 to 100 nanometers ($1.5 \times 10^{-7}$ to $1 \times 10^{-5}$ centimeters). It is believed that an average pore diameter of about 3 to 100 nanometers ($3 \times 10^{-7}$ to $1 \times 10^{-5}$ centimeters) is preferred for most CO sensor applications. Larger pores result in a less light transmittance, less surface area, and collection of dusts, dirts, and aerosols. However, the more translucent large pore sensors are useful for visual color indicating devices. Pores that are too small, on the other hand, are unable to accommodate the target gas or greatly increase diffusion time and, thus display reduced sensitivity. In a preferred embodiment of the sensor system, at least one substrate forming a Sensor has an average pore diameter of greater than about 15 nanometers ($1.5 \times 10^{-6}$ centimeters).

An improved chemical sensor system prepared according to principles of this invention comprises a sensor formed in accordance with Formula #3 disclosed above that includes: a) bromide, trichloroacetate, and trifluoroacetylacetonate ions in the chemical sensor reagent described above for Formula #2; b) surface modification of the substrate using $NH_4F$; and c) increased substrate average pore diameter from approximately 3 to 10 nanometers ($3 \times 10^{-7}$ to $1 \times 10^{-6}$ centimeters) to greater than about 15 nanometers ($1.5 \times 10^{-6}$ centimeters).

A dual sensor system that incorporates a chemical sensor prepared in accordance with Formula #1 and a second sensor prepared in accordance with Formula #2 or #3 described above meets the standards of UL 2034 at higher humidities, extends the functional lifetime of the chemical sensor system, and provides an increase in sensitivity of at least two times that of the sensor described in U.S. Pat. No. 5,063,164

(Formula #1). The chemical sensor system of this invention also responds to concentrations of CO at a more defined threshold and regenerates itself in a manner that is faster than regeneration of biological systems. For example, hemoglobin has an affinity for carbon monoxide that is about 200 times greater than its affinity for oxygen. Therefore, carbon monoxide can readily displace oxygen on hemoglobin, making the hemoglobin unable to carry oxygen. The dual sensor system of this invention reacts faster than the hemoglobin-blood-lung system of a human over a wide temperature and humidity range. The chemical sensor system also regenerates more quickly than the sensor described in U.S. Pat. No. 5,063,164 (Formula #1) upon removal of CO from the system environment.

The present invention is useful for the detection of carbon monoxide from fires, automobiles, appliances, motors, and other sources. It meets UL 2034 specifications and provides nuisance-free long life and low cost detector systems. Experimental data which verifies these statements is shown in Tables 1–9 and FIGS. 2–10, where the following definitions apply:

1. Formula #1 refers to the formula for the sensor made in accordance with U.S. Pat. No. 5,063,164.
2. Formula #1+Formula #2 refers to the dual sensor system with the first sensor 18 made in accordance with U.S. Pat. No. 5,063,164 and the second sensor 20 made with an unmodified substrate and a modified chemical sensor reagent as described herein.
3. Formula #1+Formula #3 refers to the dual sensor system first sensor 18 made in accordance with U.S. Pat. No. 5,063,164 and the second sensor 20 made with a modified substrate and a modified chemical sensor reagent as described herein.
4. $I_o$ refers to the light transmittance read by the photodiode before the sensor(s) is(are) exposed to carbon monoxide.
5. $I_f$ refers to the light transmittance read by the photodiode after the sensor(s) is(are) exposed to carbon monoxide.
6. The sensitivity, calculated as $I_o/I_f$, is one of the criterion by which the success or failure of the test is measured. These sensitivities are compared numerically in each table and graphically in figures corresponding to each table.

TABLE 1

Comparison of Sensitivities - High Humidity/Room Temperature Test
Sensors prepared in accordance with the present invention were preconditioned for 48 hours in a controlled atmosphere of 20–25° C. and 85 ± 5% relative humidity. They were then exposed to 200 ppm CO for 35 minutes under the same conditions. A sensitivity of 2.0 is a minimum requirement for passing the test. As the data below shows, only Formula #1 + Formula #3 meets this requirement. For graphical comparison see FIG. 2.

| I.D. | $I_o$ | $I_f$ |
|---|---|---|
| Formula #1 | | |
| 1 | 152.1 | 131.4 |
| 2 | 150.5 | 131.4 |
| 3 | 148.0 | 123.4 |
| 4 | 143.8 | 124.5 |
| 5 | 151.3 | 132.5 |
| 6 | 147.5 | 124.4 |
| 7 | 148.3 | 128.6 |
| 8 | 151.1 | 131.2 |
| 9 | 147.2 | 123.3 |
| 10 | 145.5 | 122.9 |
| Average | 148.5 | 127.4 |
| Std Dev | 2.7 | 4.0 |
| Average Sensitivity | | 1.2 |
| Formula #1 + Formula #2 | | |
| 1 | 118.9 | 79.9 |
| 2 | 117.7 | 80.3 |
| 3 | 122.1 | 79.6 |
| 4 | 110.9 | 102.9 |
| 5 | 121.4 | 90.8 |
| 6 | 118.2 | 86.7 |
| 7 | 124.6 | 82.3 |
| 8 | 121.0 | 94.3 |
| 9 | 119.1 | 84.1 |
| 10 | 112.0 | 93.0 |
| Average | 118.6 | 87.4 |
| Std Dev | 4.3 | 7.7 |
| Average Sensitivity | | 1.4 |
| Formula #1 + Formula #3 | | |
| 1 | 171.0 | 14.0 |
| 2 | 143.0 | 12.0 |
| 3 | 138.0 | 10.0 |
| 4 | 170.0 | 14.0 |
| 5 | 164.0 | 13.0 |
| 6 | 175.0 | 16.0 |
| 7 | 177.0 | 16.0 |
| 8 | 156.0 | 18.0 |
| 9 | 198.0 | 24.0 |
| 10 | 125.0 | 12.0 |
| Average | 161.7 | 14.9 |
| Std Dev | 21.6 | 4.0 |
| Average Sensitivity | | 10.9 |

TABLE 2

Comparison of Sensitivities - Low Humidity/Room Temperature Test
Sensors prepared in accordance with the present invention were preconditioned for 3 hours in a controlled atmosphere of 20–25° C. and 15 ± 5% relative humidity. They were then exposed to 200 ppm CO for 35 minutes under the same conditions. A sensitivity of 2.0 is a minimum requirement for passing the test. As the data below shows, Formula #1 and Formula #1 + Formula #2 just meet this requirement while Formula #1 + Formula #3 far exceeds it. For graphical comparison see FIG. 3.

| I.D. | $I_o$ | $I_f$ |
|---|---|---|
| Formula #1 | | |
| 1 | 149.6 | 72.9 |
| 2 | 145.0 | 76.9 |
| 3 | 140.8 | 72.8 |
| 4 | 157.8 | 87.3 |
| 5 | 133.8 | 71.5 |
| 6 | 134.4 | 79.0 |

TABLE 2-continued

Comparison of Sensitivities - Low Humidity/Room
Temperature Test
Sensors prepared in accordance with the present
invention were preconditioned for 3 hours in a controlled
atmosphere of 20–25° C. and 15 ± 5% relative humidity. They
were then exposed to 200 ppm CO for 35 minutes under the
same conditions. A sensitivity of 2.0 is a minimum
requirement for passing the test. As the data below
shows, Formula #1 and Formula #1 + Formula #2 just meet
this requirement while Formula #1 + Formula #3 far exceeds
it. For graphical comparison see FIG. 3.

| I.D. | $I_0$ | $I_f$ |
|---|---|---|
| 7 | 126.7 | 72.8 |
| 8 | 142.2 | 79.4 |
| 9 | 129.8 | 72.2 |
| 10 | 148.0 | 76.3 |
| Average | 140.8 | 76.1 |
| Std Dev | 9.7 | 4.9 |
| Average Sensitivity | | 1.9 |
| Formula #1 + Formula #2 | | |
| 1 | 123.9 | 55.6 |
| 2 | 123.3 | 58.8 |
| 3 | 116.8 | 62.7 |
| 4 | 122.0 | 56.8 |
| 5 | 117.9 | 46.0 |
| 6 | 127.1 | 54.5 |
| 7 | 117.3 | 47.1 |
| 8 | 137.1 | 58.2 |
| 9 | 115.9 | 58.4 |
| 10 | 112.6 | 51.6 |
| Average | 121.4 | 55.0 |
| Std Dev | 7.0 | 5.3 |
| Average Sensitivity | | 2.2 |
| Formula #1 + Formula #3 | | |
| 1 | 152.0 | 5.5 |
| 2 | 158.9 | 6.0 |
| 3 | 144.0 | 5.0 |
| 4 | 157.1 | 5.6 |
| 5 | 137.0 | 5.6 |
| 6 | 132.3 | 2.5 |
| 7 | 153.3 | 6.6 |
| 8 | 150.0 | 6.9 |
| 9 | 136.0 | 3.8 |
| 10 | 126.2 | 3.2 |
| Average | 144.7 | 5.1 |
| Std Dev | 11.3 | 1.5 |
| Average Sensitivity | | 28.5 |

TABLE 3

Comparison of Sensitivities - False Alarm (Low Level) Test
Sensors prepared in accordance with the present
invention were preconditioned for 24 hours in a controlled
atmosphere of 20–25° C. and 53 ± 3% relative humidity. They
were then exposed to 15–20 ppm CO for 8 hours under the
same conditions. A sensitivity of 1.0 is required for
passing the test, that is the sensors should not respond
to CO at all at this level. As the data below shows,
Formula #1 and Formula #1 + Formula #3 meet this
requirement while Formula #1 + Formula #2 fails. For
graphical comparison see FIG. 4.

| I.D. | $I_0$ | $I_f$ |
|---|---|---|
| Formula #1 | | |
| 1 | 150.6 | 152.4 |
| 2 | 137.7 | 139.9 |
| 3 | 145.6 | 147.4 |
| 4 | 144.0 | 146.1 |
| 5 | 144.1 | 145.2 |

TABLE 3-continued

Comparison of Sensitivities - False Alarm (Low Level) Test
Sensors prepared in accordance with the present
invention were preconditioned for 24 hours in a controlled
atmosphere of 20–25° C. and 53 ± 3% relative humidity. They
were then exposed to 15–20 ppm CO for 8 hours under the
same conditions. A sensitivity of 1.0 is required for
passing the test, that is the sensors should not respond
to CO at all at this level. As the data below shows,
Formula #1 and Formula #1 + Formula #3 meet this
requirement while Formula #1 + Formula #2 fails. For
graphical comparison see FIG. 4.

| I.D. | $I_0$ | $I_f$ |
|---|---|---|
| 6 | 152.0 | 155.1 |
| 7 | 140.6 | 141.4 |
| 8 | 142.8 | 143.5 |
| 9 | 143.5 | 143.6 |
| 10 | 133.4 | 134.5 |
| Average | 143.4 | 144.9 |
| Std Dev | 5.5 | 5.9 |
| Average Sensitivity | | 1.0 |
| Formula #1 + Formula #2 | | |
| 1 | 119.2 | 82.7 |
| 2 | 120.4 | 80.1 |
| 3 | 135.4 | 89.7 |
| 4 | 133.1 | 91.5 |
| 5 | 143.1 | 96.5 |
| 6 | 116.2 | 82.0 |
| 7 | 121.6 | 88.5 |
| 8 | 117.7 | 86.6 |
| 9 | 116.9 | 88.2 |
| 10 | 117.9 | 74.5 |
| Average | 124.2 | 86.0 |
| Std Dev | 9.5 | 6.3 |
| Average Sensitivity | | 1.4 |
| Formula #1 + Formula #3 | | |
| 1 | 55.5 | 51.1 |
| 2 | 65.2 | 59.7 |
| 3 | 50.6 | 44.9 |
| 4 | 58.1 | 54.7 |
| 5 | 56.3 | 56.4 |
| 6 | 60.6 | 59.0 |
| 7 | 64.6 | 67.8 |
| 8 | 63.8 | 61.6 |
| 9 | 73.9 | 71.7 |
| 10 | 67.8 | 62.6 |
| Average | 61.6 | 59.0 |
| Std Dev | 6.8 | 7.8 |
| Average Sensitivity | | 1.0 |

TABLE 4

Comparison of Sensitivities - High Humidity/High
Temperature Test (UL Residential Standards)
Sensors prepared in accordance with the present
invention were preconditioned for 168 hours (7 days) in a
controlled atmosphere of 52° C. and 95% relative humidity.
They were then exposed to 400 ppm CO for 15 minutes under
the same conditions. A sensitivity of 2.0 is a minimum
requirement for passing the test. As the data below
shows, Formula #1 and Formula #1 + Formula #2 fail to
meet the requirement, while Formula #1 + Formula #3 far
exceeds it. For graphical comparison see FIG. 5.

| I.D. | $I_0$ | $I_f$ |
|---|---|---|
| Formula #1 | | |
| 1 | 152.1 | 131.4 |
| 2 | 150.5 | 131.4 |
| 3 | 148.0 | 123.4 |
| 4 | 143.8 | 124.5 |
| 5 | 151.3 | 132.5 |
| 6 | 147.5 | 124.4 |

TABLE 4-continued

Comparison of Sensitivities - High Humidity/High
Temperature Test (UL Residential Standards)
Sensors prepared in accordance with the present
invention were preconditioned for 168 hours (7 days) in a
controlled atmosphere of 52° C. and 95% relative humidity.
They were then exposed to 400 ppm CO for 15 minutes under
the same conditions. A sensitivity of 2.0 is a minimum
requirement for passing the test. As the data below
shows, Formula #1 and Formula #1 + Formula #2 fail to
meet the requirement, while Formula #1 + Formula #3 far
exceeds it. For graphical comparison see FIG. 5.

| I.D. | $I_o$ | $I_f$ |
|---|---|---|
| 7 | 148.3 | 128.6 |
| 8 | 151.1 | 131.2 |
| 9 | 147.2 | 123.3 |
| 10 | 145.5 | 122.9 |
| Average | 148.5 | 127.4 |
| Std Dev | 2.7 | 4.0 |
| Average Sensitivity | | 1.2 |
| Formula #1 + Formula #2 | | |
| 1 | 116.7 | 52.1 |
| 2 | 122.2 | 89.7 |
| 3 | 102.2 | 63.6 |
| 4 | 119.2 | 49.0 |
| 5 | 121.9 | 77.1 |
| 6 | 122.4 | 65.1 |
| 7 | 132.7 | 71.1 |
| 8 | 122.5 | 66.7 |
| 9 | 123.3 | 71.5 |
| 10 | 117.3 | 78.7 |
| Average | 120.0 | 68.5 |
| Std Dev | 7.7 | 12.2 |
| Average Sensitivity | | 1.8 |
| Formula #1 + Formula #3 | | |
| 1 | 58.4 | 4.1 |
| 2 | 56.0 | 4.7 |
| 3 | 68.3 | 4.6 |
| 4 | 64.8 | 4.6 |
| 5 | 57.0 | 4.7 |
| 6 | 45.4 | 5.0 |
| 7 | 50.1 | 6.2 |
| 8 | 50.8 | 5.2 |
| 9 | 60.2 | 5.3 |
| 10 | 56.6 | 5.5 |
| Average | 56.8 | 5.0 |
| Std Dev | 6.8 | 0.6 |
| Average Sensitivity | | 11.4 |

TABLE 5

Comparison of Sensitivities - High Humidity/High
Temperature Test (UL RV Standards)
Sensors prepared in accordance with the present
invention were preconditioned for 240 hours (10 days) in
a controlled atmosphere of 61° C. and 93% relative humidity.
The relative humidity was then decreased to 85% for three
hours with subsequent exposure to 400 ppm CO for 15
minutes under the same conditions. A sensitivity of 2.0
is a minimum requirement for passing the test. As the
data below shows, there is no data for Formula #1 but it
is not expected that they would pass as they failed to
pass the high humidity residential standards (see Table
4). Formula #1 + Formula #2 also does not meet this
requirement while Formula #1 + Formula #3 far exceeds it.
Sensors that pass this test are considered suitable (by UL
standards) for use in recreational vehicles (RVs),
provided they meet all other requirements also. For
graphical comparison see FIG. 6.

| I.D. | $I_o$ | $I_f$ |
|---|---|---|
| Formula #1 | | |
| 1 | DATA | |
| 2 | NOT | |
| 3 | AVAILABLE | |
| 4 | | |
| 5 | | |
| 6 | | |
| 7 | | |
| 8 | | |
| 9 | | |
| 10 | | |
| Formula #1 + Formula #2 | | |
| 1 | 127.1 | 81.8 |
| 2 | 111.4 | 47.6 |
| 3 | 115.5 | 76.5 |
| 4 | 116.9 | 81.9 |
| 5 | 100.9 | 75.5 |
| 6 | 125.4 | 86.8 |
| 7 | 116.4 | 80.8 |
| 8 | 117.9 | 80.9 |
| 9 | 125.8 | 81.4 |
| 10 | 127.6 | 90.0 |
| Average | 118.5 | 78.3 |
| Std Dev | 8.4 | 11.6 |
| Average Sensitivity | | 1.5 |
| Formula #1 + Formula #3 | | |
| 1 | 63.3 | 5.6 |
| 2 | 58.1 | 5.1 |
| 3 | 52.1 | 4.9 |
| 4 | 59.9 | 5.3 |
| 5 | 58.7 | 4.5 |
| 6 | 42.7 | 5.9 |
| 7 | 64.2 | 6.6 |
| 8 | 52.4 | 7.7 |
| 9 | 57.0 | 7.7 |
| 10 | 49.2 | 5.7 |
| Average | 55.8 | 5.9 |
| Std Dev | 6.7 | 1.1 |
| Average Sensitivity | | 9.5 |

TABLE 6

Comparison of Sensitivities - Accelerated Aging Test
Sensors prepared in accordance with the present
invention were preconditioned for 30 days at 70° C. and low
relative humidity. The temperature and relative humidity
were then adjusted to 49° C. and 50 ± 20% for 1 hour and the
sensors subsequently exposed to 200 ppm CO for 35 minutes.
A sensitivity of 2.0 is a minimum requirement for passing
the test. As the data below shows, Formula #1 and Formula
1 + Formula #2 do not meet this requirement while Formula
1 + Formula #3 far exceeds it. For graphical comparison
see FIG. 7.

| I.D. | $I_o$ | $I_f$ |
|---|---|---|
| Formula #1 | | |
| 1 | 626.0 | 443.0 |
| 2 | 538.0 | 351.0 |
| 3 | 584.0 | 385.0 |
| 4 | 487.0 | 306.0 |
| 5 | 533.0 | 365.0 |

TABLE 6-continued

Comparison of Sensitivities - Accelerated Aging Test
Sensors prepared in accordance with the present
invention were preconditioned for 30 days at 70° C. and low
relative humidity. The temperature and relative humidity
were then adjusted to 49° C. and 50 ± 20% for 1 hour and the
sensors subsequently exposed to 200 ppm CO for 35 minutes.
A sensitivity of 2.0 is a minimum requirement for passing
the test. As the data below shows, Formula #1 and Formula
1 + Formula #2 do not meet this requirement while Formula
1 + Formula #3 far exceeds it. For graphical comparison
see FIG. 7.

| I.D. | $I_o$ | $I_r$ |
|---|---|---|
| 6 | 545.0 | 348.0 |
| 7 | 665.0 | 443.0 |
| 8 | 633.0 | 430.0 |
| 9 | 585.0 | 392.0 |
| 10 | 525.0 | 390.0 |
| Average | 572.1 | 385.3 |
| Std Dev | 56.2 | 44.7 |
| Average Sensitivity | | 1.5 |
| Formula #1 + Formula #2 | | |
| 1 | 663.0 | 142.0 |
| 2 | 569.0 | 118.0 |
| 3 | 688.0 | 102.0 |
| 4 | 614.0 | 131.0 |
| 5 | 563.0 | 97.0 |
| 6 | 657.0 | 145.0 |
| 7 | 542.0 | 117.0 |
| 8 | 650.0 | 112.0 |
| 9 | 620.0 | 68.0 |
| 10 | 617.0 | 110.0 |
| Average | 618.3 | 114.2 |
| Std Dev | 47.9 | 22.7 |
| Average Sensitivity | | 1.5 |
| Formula #1 + Formula #3 | | |
| 1 | 469.0 | 54.0 |
| 2 | 578.0 | 34.0 |
| 3 | 550.0 | 36.0 |
| 4 | 529.0 | 38.0 |
| 5 | 533.0 | 37.0 |
| 6 | 509.0 | 58.0 |
| 7 | 507.0 | 49.0 |
| 8 | 511.0 | 32.0 |
| 9 | 492.0 | 32.0 |
| 10 | 480.0 | 24.0 |
| Average | 515.8 | 39.4 |
| Std Dev | 32.8 | 10.8 |
| Average Sensitivity | | 13.1 |

TABLE 7

Comparison of Sensitivities - Low Humidity/Low
Temperature Test
Sensors prepared in accordance with the present
invention were preconditioned for 72 hours in a controlled
atmosphere of −40° C. and low relative humidity. The
temperature and relative humidity were then increased to
0° C. and 15 ± 5% and the sensors subsequently exposed to 200
ppm CO for 35 minutes. A sensitivity of 2.0 is a minimum
requirement for passing the test. While there is no data
for Formula #1, the data below shows that both Formula #1 +
Formula #2 and Formula #1 + Formula #3 far exceed this
requirement. For graphical comparison see FIG. 8.

| I.D. | $I_o$ | $I_r$ |
|---|---|---|
| Formula #1 | | |
| 1 | DATA | |
| 2 | NOT | |
| 3 | AVAILABLE | |
| 4 | | |
| 5 | | |

TABLE 7-continued

Comparison of Sensitivities - Low Humidity/Low
Temperature Test
Sensors prepared in accordance with the present
invention were preconditioned for 72 hours in a controlled
atmosphere of −40° C. and low relative humidity. The
temperature and relative humidity were then increased to
0° C. and 15 ± 5% and the sensors subsequently exposed to 200
ppm CO for 35 minutes. A sensitivity of 2.0 is a minimum
requirement for passing the test. While there is no data
for Formula #1, the data below shows that both Formula #1 +
Formula #2 and Formula #1 + Formula #3 far exceed this
requirement. For graphical comparison see FIG. 8.

| I.D. | $I_o$ | $I_r$ |
|---|---|---|
| 6 | | |
| 7 | | |
| 8 | | |
| 9 | | |
| 10 | | |
| Average | | |
| Std Dev | | |
| Average Sensitivity | | |
| Formula #1 + Formula #2 | | |
| 1 | 126.6 | 9.5 |
| 2 | 133.7 | 10.4 |
| 3 | 125.4 | 10.0 |
| 4 | 120.6 | 9.0 |
| 5 | 120.6 | 11.8 |
| 6 | 120.1 | 8.1 |
| 7 | 111.9 | 8.6 |
| 8 | 124.6 | 12.3 |
| 9 | 125.9 | 11.7 |
| 10 | 125.4 | 10.7 |
| Average | 123.5 | 10.2 |
| Std Dev | 5.7 | 1.4 |
| Average Sensitivity | | 12.1 |
| Formula #1 + Formula #3 | | |
| 1 | 60.0 | 3.6 |
| 2 | 74.9 | 4.5 |
| 3 | 62.0 | 4.3 |
| 4 | 60.8 | 5.1 |
| 5 | 65.4 | 4.6 |
| 6 | 65.5 | 4.1 |
| 7 | 58.2 | 4.1 |
| 8 | 66.8 | 4.6 |
| 9 | 66.3 | 4.7 |
| 10 | 60.3 | 4.3 |
| Average | 64.0 | 4.4 |
| Std Dev | 4.9 | 0.4 |
| Average Sensitivity | | 14.6 |

TABLE 8

Comparison of Sensitivities - Standard CO Test
Sensors prepared in accordance with the present
invention were preconditioned for 24 hours in a controlled
atmosphere of 20–25° C. and 53 ± 2% relative humidity. They
were then exposed to 100 ppm CO for 80 minutes under
ambient conditions. A sensitivity of 2.0 is a minimum
requirement for passing the test. As the data below
shows, Formula #1 does not meet this requirement, while
Formula #1 + Formula #2 and Formula #1 + Formula #3 pass
with equal sensitivities. For graphical comparison see FIG. 9.

| I.D. | $I_o$ | $I_r$ |
|---|---|---|
| Formula #1 | | |
| 1 | 147.2 | 96.0 |
| 2 | 141.4 | 93.3 |
| 3 | 137.3 | 92.5 |
| 4 | 154.1 | 102.3 |
| 5 | 141.5 | 94.9 |
| 6 | 132.1 | 88.0 |

TABLE 8-continued

Comparison of Sensitivities - Standard CO Test
Sensors prepared in accordance with the present
invention were preconditioned for 24 hours in a controlled
atmosphere of 20–25° C. and 53 ± 2% relative humidity. They
were then exposed to 100 ppm CO for 80 minutes under
ambient conditions. A sensitivity of 2.0 is a minimum
requirement for passing the test. As the data below
shows, Formula #1 does not meet this requirement, while
Formula #1 + Formula #2 and Formula #1 + Formula #3 pass
with equal sensitivities. For graphical comparison see FIG. 9.

| I.D. | $I_0$ | $I_f$ |
|---|---|---|
| 7 | 132.6 | 89.6 |
| 8 | 124.7 | 82.5 |
| 9 | 140.1 | 90.0 |
| 10 | 127.7 | 73.9 |
| Average | 137.9 | 90.3 |
| Std Dev | 8.9 | 7.8 |
| Average Sensitivity | | 1.5 |
| Formula #1 + Formula #2 | | |
| 1 | 131.0 | 40.9 |
| 2 | 129.5 | 38.6 |
| 3 | 123.9 | 37.9 |
| 4 | 133.6 | 44.5 |
| 5 | 125.7 | 40.1 |
| 6 | 128.8 | 40.4 |
| 7 | 118.8 | 42.6 |
| 8 | 120.3 | 41.0 |
| 9 | 129.3 | 40.5 |
| 10 | 128.9 | 43.1 |
| Average | 127.0 | 43.0 |
| Std Dev | 4.7 | 2.0 |
| Average Sensitivity | | 3.0 |
| Formula #1 + Formula #3 | | |
| 1 | 67.8 | 22.7 |
| 2 | 65.7 | 20.9 |
| 3 | 67.4 | 22.4 |
| 4 | 68.3 | 23.9 |
| 5 | 68.6 | 22.1 |
| 6 | 63.0 | 22.2 |
| 7 | 51.5 | 18.0 |
| 8 | 84.2 | 27.2 |
| 9 | 56.3 | 17.9 |
| 10 | 59.8 | 16.9 |
| Average | 65.3 | 21.4 |
| Std Dev | 8.8 | 3.1 |
| Average Sensitivity | | 3.0 |

TABLE 9

Comparison of Regeneration Rates - Standard CO Test
This is the same data presented in Table 2. The
numbers in the additional column with the heading $I_1$ refer
to the light transmittance read by the photodiode 24 hours
after the sensors were exposed to carbon monoxide. The
shaded area at the bottom of the table gives the %
regeneration of the sensor. This is calculated as $((I_1 - I_f)/(I_0 - I_f)) \times 100$. A regeneration rate of 90% at 24 hours
after exposure to carbon monoxide is a minimum standard
for passing this test. As the data shows, all three
formulations regenerated easily after 24 hours. For
graphical comparison see FIG. 10.

| I.D. | $I_0$ | $I_f$ | $I_1$ |
|---|---|---|---|
| Formula #1 | | | |
| 1 | 147.2 | 96.0 | 143.7 |
| 2 | 141.4 | 93.3 | 138.6 |
| 3 | 137.3 | 92.5 | 134.7 |
| 4 | 154.1 | 102.3 | 152.9 |
| 5 | 141.5 | 94.9 | 143.3 |
| 6 | 132.1 | 88.0 | 130.8 |
| 7 | 132.6 | 89.6 | 131.3 |

TABLE 9-continued

Comparison of Regeneration Rates - Standard CO Test
This is the same data presented in Table 2. The
numbers in the additional column with the heading $I_1$ refer
to the light transmittance read by the photodiode 24 hours
after the sensors were exposed to carbon monoxide. The
shaded area at the bottom of the table gives the %
regeneration of the sensor. This is calculated as $((I_1 - I_f)/(I_0 - I_f)) \times 100$. A regeneration rate of 90% at 24 hours
after exposure to carbon monoxide is a minimum standard
for passing this test. As the data shows, all three
formulations regenerated easily after 24 hours. For
graphical comparison see FIG. 10.

| I.D. | $I_0$ | $I_f$ | $I_1$ |
|---|---|---|---|
| 8 | 124.7 | 82.5 | 120.3 |
| 9 | 140.1 | 90.0 | 136.1 |
| 10 | 127.7 | 73.9 | 119.6 |
| Avg | 137.9 | 90.3 | 135.1 |
| SD | 8.9 | 7.8 | 10.33 |
| Avg. Sens. | | 1.5 | |
| % Regen. | | | 94.22 |
| Formula #1 + Formula #2 | | | |
| 1 | 131.0 | 40.9 | 123.5 |
| 2 | 129.5 | 38.6 | 120.0 |
| 3 | 123.9 | 37.9 | 117.3 |
| 4 | 133.6 | 44.5 | 123.3 |
| 5 | 125.7 | 40.1 | 117.2 |
| 6 | 128.8 | 40.4 | 119.3 |
| 7 | 118.8 | 42.6 | 111.3 |
| 8 | 120.3 | 41.0 | 113.8 |
| 9 | 129.3 | 40.5 | 120.5 |
| 10 | 128.9 | 43.1 | 121.5 |
| Avg | 127.0 | 43.0 | 118.8 |
| SD | 4.7 | 2.0 | 3.9 |
| Avg. Sens. | | 3.0 | |
| % Regen. | | | 90.22 |
| Formula #1 + Formula #3 | | | |
| 1 | 67.8 | 22.7 | 64.2 |
| 2 | 65.7 | 20.9 | 61.5 |
| 3 | 67.4 | 22.4 | 63.9 |
| 4 | 68.3 | 23.9 | 64.9 |
| 5 | 68.6 | 22.1 | 64.7 |
| 6 | 63.0 | 22.2 | 59.5 |
| 7 | 51.5 | 18.0 | 48.7 |
| 8 | 84.2 | 27.2 | 80.4 |
| 9 | 56.3 | 17.9 | 53.4 |
| 10 | 59.8 | 16.9 | 55.8 |
| Avg | 65.3 | 21.4 | 61.7 |
| SD | 8.8 | 3.1 | 8.5 |
| Avg. Sens. | | 3.0 | |
| % Regen. | | | 91.9 |

DESCRIPTION OF PREFERRED EMBODIMENTS

Surface modified VYCOR® glass was prepared by soaking porous VYCOR® disks 0.100" thick and ¼" in diameter in a 12–20% solution of ammonium fluoride for 2 hours at 55° C. The disks were then rinsed briefly and cooked further at 55° C. for 11–20 hours. This was followed by rinsing in water for several hours and drying by heating at 400° C. for 4 hours.

Biomimetic sensors were prepared by soaking pieces of porous VYCOR® glass or surface-modified VYCOR® glass for four days in the solutions described in the examples below. The sensors formed from impregnated VYCOR° glass were then, in turn, air-dried at 20°–25° C. and heated to 40° C., each time for 18–24 hours. Measurements of the optical density of the prepared chemical sensor systems before and after exposure to carbon monoxide were made using standard laboratory instruments.

EXAMPLE 1

Preparation of Sensor #1

50 porous VYCOR® disks were soaked in a solution prepared according to the following recipe: $1.504 \times 10^{-6}$ moles $H_4Mo_{12}SiO_{40}$ in 35 mL $H_2O$; $3.324 \times 10^{-2}$ moles $CaCl_2 \cdot 2H_2O$; $6.713 \times 10^{-4}$ moles g $Na_2PdCl_4$; $4.075 \times 10^{-4}$ moles β-cyclodextrin; $3.346 \times 10^{-4}$ moles $CuCl_2 \cdot 2H_2O$; $3.045 \times 10^{-4}$ moles γ-cyclodextrin; $9.588 \times 10^{-3}$ moles $PdCl_2$; and sufficient $H_2O$, to bring total solution volume to 100.00 mL.

EXAMPLE 2

Preparation of Sensor #2

50 porous VYCOR® disks were soaked in an aqueous solution of 12.5% $NH_4F$, then cooked for 17 hours at 55° C. They were then rinsed thoroughly and dried in a furnace at 400° C. The modified disks were then soaked in a reagant solution prepared according to the following recipe: $1.205 \times 10^{-6}$ moles $H_4Mo_{12}SiO_{40}$ in 40 mL $H_2O$; $4.034 \times 10^{-4}$ moles γ-cyclodextrin; $5.642 \times 10^{-4}$ moles $Na_2PdCl_4$; $5.712 \times 10^{-4}$ moles $CuCl_2 \cdot 2H_2O$; $7.742 \times 10^{-3}$ moles $CaBr_2 \cdot H_2O$; $2.282 \times 10^{-2}$ moles $CaCl_2 \cdot 2H_2O$; $2.261 \times 10^{-3}$ moles $Cl_3CCO_2H$; $1.301 \times 10^{-4}$ moles $Cu(H_3CCOCHCOCF_3)_2$; $8.082 \times 10^{-4}$ moles Hβ-cyclodextrin; $5.523 \times 10^{-3}$ moles $PdCl_2$; and sufficient $H_2O$, to bring total solution volume to 100.00 mL.

A number of different ways exist to combine the sensors. These include the use of fiber optics, reflectors, lenses, or combinations thereof, in addition to the standard method shown in FIG. 1.

The data presented in Tables 1–8 demonstrate the superior response of sensors prepared in accordance with principles of this invention, with additives and modified substrates, over sensors developed in accordance with U.S. Pat. No. 5,063,164. The data clearly shows improvement in the response at high humidity; however the new sensor does not by itself pass paragraph 44.1 which states that sensors must be conditioned at 0° C. with relative humidity of 15±5% for at least three hours before CO exposure and that sensors must set alarms off within a given amount of time under certain CO concentrations. The yellow sensor, however does respond to CO after extended dry humidity exposure.

Moreover, the sensors prepared according to principles of this invention also pass the severe aging conditions specified in UL 2034 paragraph 68. The new sensors pass the 30 days at 66° C., 3 days at −40° C., and 7 days at 62° C. with relative humidity of 93±2%, whereas the sensor from U.S. Pat. No. 5,063,164 does not even pass the 30 days at 66° C. It is through the combination of the two sensors, according to principles of this invention, that the carbon monoxide sensor system can pass the conditions specified in the UL 2034 published Apr. 30, 1992.

The improved chemical sensor system prepared according to principles of this invention have been specifically described and illustrated in relation to limited working embodiments for purposes of clarity and illustration. Many modifications and variations will be apparent to those skilled in the art. Accordingly, it is to be understood that, within the scope of the appended claims, the improved chemical sensor system prepared according to principles of this invention may be embodied other than as specifically described herein.

What is claimed is:

1. A biomimetic sensor system comprising:
   at least two photon absorbing/transmitting organometallic sensors for detecting the presence of airborne carbon monoxide, wherein at least one sensor includes:
   a first sensor substrate formed from a porous semi-transparent material, wherein the first sensor substrate has an average pore diameter of greater than 15 nanometers; and
   a first self-regenerating chemical sensor reagent for detecting carbon monoxide, wherein the first self-regenerating chemical sensor reagent is impregnated into the first substrate and includes at least one compound selected from each of the following groups:
   Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$, $PdCl_2 \cdot 2H_2O$, $PdBr_2 \cdot 2H_2O$, $K_2PdBr_4$, $Na_2PdBr_4$, $PdCl_2Br_2^{-2}$, $PdCl_3Br^{-2}$, $PdClBr_3^{-2}$, and mixtures thereof;
   Group 2—molybdenum selected from the group consisting of silicomolybdic acid, salts of silicomolybdic acid, molybdenum trioxide, heteropolyacids of molybdenum containing vanadium, copper or tungsten, ammonium molybdate, alkali metal or alkaline earth salts of the molybdate anion, heteropolymolybdates and mixtures thereof;
   Group 3—copper salts selected from the group consisting of copper sulfate, copper bromide, copper chloride, copper fluoride, copper iodide, and copper perchlorate;
   Group 4—molecular encapsulants selected from the group consisting of α-cyclodextrin, β-cyclodextrin, modified β-cyclodextrin, and γ-cyclodextrin and mixtures thereof;
   Group 5—soluble chloride and bromide ions selected from the group consisting of lithium, sodium, platinum, calcium, magnesium, and cobalt chlorides and bromides, and mixtures thereof; and
   Group 6—an organic solvent and trifluorinated organic anion, the solvent selected from the group consisting of dimethyl sulfoxide, tetrahydrofuran, dimethyl formamide, trichloroacetic acid, and the anion is a soluble metal trifluoroacetylacetonate selected from the cation group consisting of copper, calcium, magnesium, sodium, potassium, and lithium, and mixtures thereof.

2. A biomimetic sensor system as recited in claim 1 wherein the first chemical sensor reagent includes compounds from groups 1 through 6 that are present in mole ratio ranges of: group 1: group 2=0.01:1 to 0.5:1; group 3: group 2=0.001:1 to 0.08:1; group 4: group 2=1:1 to 20:1; group 5: group 2=0.01:1 to 10:1; and group 6: group 2=0.00001:1 to 0.001:1.

3. A biomimetic sensor system as recited in claim 1 further comprising a second self-regenerating chemical sensor, said second self-regenerating chemical sensor comprises:
   a second sensor substrate formed from a porous semi-transparent material, wherein the second substrate has an average pore diameter in the range from about 3 to 100 nanometers, and a second self-regenerating chemical sensor reagent for detecting carbon monoxide, wherein the second self-regenerating chemical sensor reagent is impregnated into the second substrate and includes at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2—molybdenum or tungsten salts or acid salts selected from the group consisting of silicomolybdic acid, salts of silicomolybdic acid, molybdenum trioxide, heteropolyacids of molybdenum, ammonium molybdate, alkali metal, or alkaline earth metal salts of the molybdate anion, mixed heteropolymolybdates, and heteropolytungstates;

Group 3—copper salts selected from the group consisting of copper sulfate, copper chloride, copper bromide, copper iodide, and copper perchlorate;

Group 4—molecular encapsulants selected from the group consisting of α-cyclodextrin, β-cyclodextrin, modified β-cyclodextrin, and γ-cyclodextrin; and Group 5—soluble chloride ions selected from the group consisting of lithium chloride, sodium chloride, lithium perchlorate, aluminum perchlorate, platinum chloride, inorganic acids, calcium chloride, magnesium chloride, cobalt chloride and mixtures thereof.

4. A biomimetic sensor system as recited in claim 3 wherein the first and second sensor substrates are selected from the group consisting of porous silica gel beads, porous leached borosilicate glass, porous leached borosilicate glass that has been treated with ammonium fluoride, porous silicon dioxides, porous aluminosilicates, alumina, titanium dioxide and aluminum titanium oxides.

5. A biomimetic sensor system as recited in claim 3, further comprising a sensor housing for optically combining the first and second sensors between a light source and a light detection means.

6. A biomimetic sensor system as recited in claim 5 wherein the first and second sensors are arranged serially in a light path between the light source and the light detection means.

7. A biomimetic sensor system as recited in claim 5 wherein the first sensor is adapted to respond to carbon monoxide under conditions of high relative humidity, and the second sensor is adapted to respond to carbon monoxide under conditions of low relative humidity.

8. A biomimetic sensor system as recited in claim 7 wherein the combination of sensors allows the system to meet the criteria of UL 2034 published on Apr. 30, 1992.

9. A biomimetic sensor system as recited in claim 1 wherein the at least one compound from group 1 is palladium chloride and $Na_2PdCl_4$, the at least one compound from group 2 is silicomolybdic acid, the at least one compound from group 3 is copper chloride, the at least one compound from group 4 is a modified β-cyclodextrin and γ-cyclodextrin, the at least one compound from group 5 is calcium chloride and calcium bromide, and the at least one compound from group 6 is trichloroacetic acid and copper trifluoroacetylacetonate.

10. A biomimetic sensor system comprising:

at least two photon absorbing/transmitting organometallic sensors for detecting the presence of airborne carbon monoxide, the sensors being optically combined in a housing between a light source and a light detecting means and wherein at least one first sensor includes:

a first sensor substrate formed from a porous semi-transparent material that is at least partially transmissive to the near infrared light band and has an average surface pore diameter greater than about 15 nanometers; and a first self-regenerating chemical sensor reagent for detecting carbon monoxide, wherein the first self-regenerating chemical sensor reagent is impregnated into the first substrate and is a mixture including at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$, $PdCl_2 \cdot 2H_2O$, $PdBr_2 \cdot 2H_2O$, $K_2PdBr_4$, $Na_2PdBr_4$, $PdCl_2Br_2^{-2}$, $PdCl_3Br^{-2}$, $PdClBr_3^{-2}$, and mixtures thereof;

Group 2—molybdenum selected from the group consisting of silicomolybdic acid, salts of silicomolybdic acid, molybdenum trioxide, heteropolyacids of molybdenum containing vanadium, copper or tungsten, ammonium molybdate, alkali metal or alkaline earth salts of the molybdate anion, heteropolymolybdates and mixtures thereof;

Group 3—copper salts selected from the group consisting of copper sulfate, copper bromide, Copper chloride, copper fluoride, copper iodide, and copper perchlorate;

Group 4—molecular encapsulants selected from the group consisting of α-cyclodextrin, β-cyclodextrin, modified β-cyclodextrin, and γ-cyclodextrin and mixtures thereof;

Group 5—soluble chloride and bromide ions selected from the group consisting of lithium, sodium, platinum, calcium, magnesium, and cobalt chlorides and bromides, and mixtures thereof; and Group 6—an organic solvent and trifluorinated organic anion, the solvent selected from the group consisting of dimethyl sulfoxide, tetrahydrofuran, dimethyl formamide, trichloroacetic acid, and the anion is a soluble metal trifluoroacetylacetonate selected from the cation group consisting of copper, calcium, magnesium, sodium, potassium, and lithium, and mixtures thereof.

11. A biomimetic sensor system as recited in claim 10 further comprising a second chemical sensor, said second chemical sensor includes:

a second sensor substrate formed from a porous semi-transparent material that is at least partially transmissive to the near infrared light band and has an average surface pore diameter in the range of from about 3 to 100 nanometers, and a second self-regenerating chemical sensor reagent for detecting carbon monoxide, wherein the second self-regenerating chemical sensor reagent is impregnated into the second substrate and includes at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2—molybdenum or tungsten salts or acid salts selected from the group consisting of silicomolybdic acid, salts of silicomolybdic acid, molybdenum trioxide, heteropolyacids of molybdenum, ammonium molybdate, alkali metal, or alkaline earth metal salts of the molybdate anion, mixed heteropolymolybdates, and heteropolytungstates;

Group 3—copper salts selected from the group consisting of copper sulfate, copper chloride, copper bromide, copper iodide, and copper perchlorate;

Group 4—molecular encapsulants selected from the group consisting of α-cyclodextrin, β-cyclodextrin, modified β-cyclodextrin, and γ-cyclodextrin; and Group 5—soluble chloride ions selected from the group consisting of lithium chloride, sodium chloride, lithium perchlorate, aluminum perchlorate, platinum chloride, inorganic acids, calcium chloride, magnesium chloride, cobalt chloride and mixtures thereof.

12. A biomimetic sensor system as recited in claim 11 wherein the first and second sensor substrates are selected from the group consisting of porous silica gel beads, porous leached borosilicate glass, porous leached borosilicate glass that has been treated with ammonium fluoride, porous silicon dioxides, porous aluminosilicates, alumina, titanium dioxide, and aluminum titanium oxides.

13. A biomimetic sensor system as recited in claim 11 wherein the combination of sensors permits the sensor system to meet the criteria as set out in UL 2034 published on Apr. 30, 1992.

14. A biomimetic sensor system as recited in claim 10 wherein the first sensor is adapted to respond optimally to carbon monoxide under conditions of high relative humidity, and the second sensor is adapted to respond optimally to carbon monoxide under conditions of low relative humidity.

15. A biomimetic sensor system as recited in claim 14 wherein the two sensors are serially aligned by the housing in a light path between a light source and a light detection means.

16. A self-regenerating biomimetic carbon monoxide sensor comprising:

a porous semi-transparent substrate having an average pore diameter greater than about 15 nanometers; and, a self-regenerating chemical sensor reagent for detecting airborne toxins impregnated into the substrate, wherein the chemical sensor reagent includes at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$, $PdCl_2.2H_2O$, $PdBr_2.2H_2O$, $K_2PdBr_4$, $Na_2PdBr_4$, $PdCl_2Br_2^{-2}$, $PdCl_3Br^{-2}$, $PdClBr_3^{-2}$, and mixtures thereof;

Group 2—molybdenum selected from the group consisting of silicomolybdic acid, salts of silicomolybdic acid, molybdenum trioxide, heteropolyacids of molybdenum containing vanadium, copper or tungsten, ammonium molybdate, alkali metal or alkaline earth salts of the molybdate anion, heteropolymolybdates and mixtures thereof;

Group 3—copper salts selected from the group consisting of copper sulfate, copper bromide, copper chloride, copper fluoride, copper iodide, and copper perchlorate;

Group 4—molecular encapsulants selected from the group consisting of α-cyclodextrin, β-cyclodextrin, modified β-cyclodextrin, and γ-cyclodextrin and mixtures thereof;

Group 5—soluble chloride and bromide ions selected from the group of lithium, sodium, platinum, calcium, magnesium, and cobalt chlorides and bromides, and mixtures thereof; and Group 6—an organic solvent and trifluorinated organic anion, the solvent being selected from the group consisting of dimethyl sulfoxide, tetrahydrofuran, dimethyl formamide, and trichloroacetic acid, and the anion being a soluble metal trifluoroacetylacetonate selected from the cation group consisting of copper, calcium, magnesium, sodium, potassium, and lithium, and mixtures thereof.

17. The self-regenerating carbon monoxide sensor system as recited in claim 16 wherein the porous semi-transparent substrate is selected from the group consisting of porous silica gel beads, porous leached borosilicate glass, porous leached borosilicate glass that has been treated with ammonium fluoride, porous silicon dioxides, porous aluminosilicates, alumina, titanium dioxide and, aluminum titanium oxides.

18. A self-regenerating carbon monoxide sensor as recited in claim 16 wherein the porous semi-transparent substrate has an average surface pore diameter greater than about 15 nanometers.

19. The self-regenerating biomimetic carbon monoxide sensor system as recited in claim 16 wherein the chemical sensor reagent includes compounds from groups 1 through 6 that are present in the mole ratio ranges of: group 1:group 2=0.01:1 to 0.5:1; group 3: group 2=0,001:1 to 0.08:1; group 4:group 2=1:1 to 20:1; group 5:group 2=0.01:1 to 10:1; and group 6:group 2=0.00001:1 to 0.001:1.

20. The self-regenerating biomimetic carbon monoxide sensor system as recited in claim 19 wherein the at least one compound from group 1 is palladium chloride and $Na_2PdCl_4$, the at least one compound from group 2 is silicomolybdic acid, the at least one compound from group 3 is copper chloride, the at least one compound from group 4 is modified β-cyclodextrin and γ-cyclodextrin, the at least one compound from group 5 is calcium chloride and calcium bromide, and the at least one compound from group 6 is trichloroacetic acid and copper trifluoroacetylacetonate.

21. A self-regenerating sensor system for detecting the presence of carbon monoxide comprising:

at least two sensors that are at least partially transmissive to the near infrared light band, wherein a first self-regenerating sensor comprises:

a first porous, semi-transparent substrate, a first self-regenerating chemical sensor reagent impregnated into the first substrate, wherein the first self-regenerating chemical sensor reagent is a mixture of chemical compounds including at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$ and $K_2PdCl_4$;

Group 2—molybdenum or tungsten salts or acid salts selected from the group consisting of silicomolybdic acid, salts of silicomolybdic acid, molybdenum trioxide, heteropolyacids of molybdenum, ammonium molybdate, alkali metal, or alkaline earth metal salts of the molybdate anion, mixed heteropolymolybdates, and heteropolytungstates;

Group 3—copper salts selected from the group consisting of copper sulfate, copper chloride, copper bromide, copper iodide, and copper perchlorate;

Group 4—molecular encapsulants selected from the group consisting of α-cyclodextrin, β-cyclodextrin, modified β-cyclodextrin, and γ-cyclodextrin; and Group 5—soluble chloride ions selected from the group consisting of lithium chloride, sodium chloride, lithium perchlorate, aluminum perchlorate, platinum chloride, inorganic acids, calcium chloride, magnesium chloride, cobalt chloride and mixtures thereof;

and wherein the first sensor is able to regenerate itself for a period of at least one year at ambient conditions, and has an optimal sensitivity to carbon monoxide under conditions of low relative humidity; and wherein a second self-regenerating sensor comprises:

a second porous, semi-transparent substrate, a second self-regenerating chemical sensor reagent impregnated into the second substrate, wherein the second self-regenerating chemical sensor reagent is a mixture of chemical compounds including at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$, $PdCl_2.2H_2O$, $PdBr_2.2H_2O$, $K_2PdBr_4$, $Na_2PdBr_4$, $PdCl_2Br_2^-$ $2PdCl_3Br^{-2}$, $PdClBr_3^{-2}$, and mixtures thereof;

Group 2—molybdenum selected from the group consisting of silicomolybdic acid, salts of silicomolybdic acid, molybdenum trioxide, heteropolyacids of molybdenum containing vanadium, copper or tungsten, ammonium molybdate, alkali metal or alkaline earth salts of the molybdate anion, heteropolymolybdates and mixtures thereof;

Group 3—copper salts selected from the group consisting of copper sulfate, copper bromide, copper chloride, copper fluoride, copper iodide, and copper perchlorate;

Group 4—molecular encapsulants selected from the group consisting of α-cyclodextrin, β-cyclodextrin, modified β-cyclodextrin, and γ-cyclodextrin and mixtures thereof;

Group 5—soluble chloride and bromide ions selected from the group consisting of lithium, sodium, aluminum, platinum, calcium, magnesium, and cobalt chlorides and bromides, and mixtures thereof; and Group 6—an organic solvent and trifluorinated organic anion, the solvent selected from the group consisting of dimethyl sulfoxide, tetrahydrofuran, dimethyl formamide, trichloroacetic acid, and the anion is a soluble metal trifluoroacetylacetonate selected from the cation group consisting of copper, calcium, magnesium, sodium, potassium, and lithium, and mixtures thereof;

and wherein the second sensor is able to regenerate itself for a period of at least one year at ambient conditions, and has an optimal sensitivity to carbon monoxide under conditions of high relative humidity;

means for aligning the first and second sensors in a light path; and, means for detecting changes in the transmission or reflection of light by the first and second sensors.

22. A self-regenerating sensor system for detecting the presence of carbon monoxide as recited in claim 21 wherein the first porous, semi-transparent substrate has an average pore diameter in the range of about 3 to 100 nanometers.

23. A self-regenerating sensor system for detecting the presence of carbon monoxide as recited in claim 21 wherein the second porous, semi-transparent substrate has an average pore diameter greater than about 15 nanometers.

24. A self-regenerating sensor system for detecting the presence of carbon monoxide as recited in claim 21 wherein the self-regenerating sensor system satisfies UL 2034 published on Apr. 30, 1992.

25. A self-regenerating biomimetic sensor system for detecting the presence of carbon monoxide as recited in claim 24 wherein the first and second sensors are arranged serially between a light source and a light detection device.

26. A self-regenerating sensor system for detecting the presence of carbon monoxide as recited in claim 21 wherein the second chemical sensor reagent includes compounds from Groups 1 through Group 6 that are present in the molar ratio ranges of: Group 1:Group 2=0.01:1 to 0.5:1; Group 3:Group 2=0.001:1 to 0.08:1; Group 4:Group 2=1:1 to 20:1; Group 5:Group 2=0.01:1 to 10:1; and Group 6:Group 2=0.00001:1 to 0.001:1.

27. A self-regenerating sensor system for detecting the presence of carbon monoxide as recited in claim 26 wherein the at least one compound from Group 1 is palladium chloride and $Na_2PdCl_4$, the at least one compound from Group 2 is silicomolybdic acid, the at least one compound from Group 3 is copper chloride, the at least one compound from Group 4 is modified β-cyclodextrin and γ-cyclodextrin, the at least one compound from Group 5 is calcium chloride and calcium bromide, and the at least one compound from Group 6 is trichloroacetic acid and copper trifluoroacetylacetonate.

28. A carbon monoxide sensor, comprising:

a porous substrate that is at least partially transmissive to near infrared light;

a chemical sensor reagent impregnated into the substrate, the reagent comprising at least one compound selected from each of the following groups:

Group 1—palladium salts selected from the group consisting of palladium sulfate, palladium sulfite, palladium pyrosulfite, palladium chloride, palladium bromide, palladium iodide, palladium perchlorate, $CaPdCl_4$, $Na_2PdCl_4$, $K_2PdCl_4$, $PdCl_2.2H_2O$, $PdBr_2.2H_2O$, $K_2PdBr_4$, $Na_2PdBr_4$, $PdCl_2Br_2^{-2}$, $PdCl_3Br^{-2}$, $PdClBr_3^{-2}$, and mixtures thereof;

Group 2—molybdenum selected from the group consisting of silicomolybdic acid, salts of silicomolybdic acid, molybdenum trioxide, heteropolyacids of molybdenum containing vanadium, copper or tungsten, ammonium molybdate, alkali metal or alkaline earth salts of the molybdate anion, heteropolymolybdates and mixtures thereof;

Group 3—copper salts selected from the group consisting of copper sulfate, copper bromide, copper chloride, copper fluoride, copper iodide, and copper perchlorate;

Group 4—molecular encapsulants selected from the group consisting of α-cyclodextrin, β-cyclodextrin, modified β-cyclodextrin, and γ-cyclodextrin and mixtures thereof;

Group 5—soluble chloride and bromide ions selected from the group consisting of lithium, sodium, aluminum, platinum, calcium, magnesium, and cobalt chlorides and bromides, and mixtures thereof; and Group 6—an organic solvent and trifluorinated organic anion, the solvent selected from the group consisting of dimethyl sulfoxide, tetrahydrofuran, dimethyl formamide, trichloroacetic acid, and the anion is a soluble metal trifluoroacetylacetonate selected from the cation group consisting of copper, calcium, magnesium, sodium, potassium, and lithium, and mixtures thereof.

29. A carbon monoxide sensor as recited in claim 28, wherein the at least one compound from Group 1 is palladium chloride and $Na_2PdCl_4$, the at least one compound from Group 2 is silicomolybdic acid, the compound from Group 3 is copper chloride, the at least one compound from Group 4 is modified β-cyclodextrin and γ-cyclodextrin, the at least one compound from Group 5 is calcium chloride and calcium bromide, and the compound from Group 6 is trichloroacetic acid and copper trifluoroacetylacetonate.

30. A carbon monoxide sensor as recited in claim 28, wherein the chemical sensor reagent includes compounds from Groups 1 through Group 6 that are present in the molar ratio ranges of: Group 1:Group 2=0.01:1 to 0.5:1; Group 3:Group 2=0.001:1 to 0.08:1; Group 4:Group 2=1:1 to 20:1; Group 5:Group 2=0.01:1 to 10:1; and Group 6:Group 2=0.00001:1 to 0.001:1.

31. A carbon monoxide sensor as recited in claim 28, wherein the substrate is selected from the substrate is selected from the group consisting of porous silica gel beads, porous leached borosilicate glass, porous leached borosilicate glass that has been treated with ammonium fluoride, porous silicon dioxides, porous aluminosilicates, alumina, titanium dioxide and aluminum titanium oxides.

* * * * *